United States Patent
Xi

(10) Patent No.: US 8,165,667 B2
(45) Date of Patent: Apr. 24, 2012

(54) METHODS AND SYSTEMS FOR OPTIMIZING EXERCISE COMPLIANCE DIAGNOSTIC PARAMETERS

(75) Inventor: Cecilia Qin Xi, Sunnyvale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 78 days.

(21) Appl. No.: 12/884,033

(22) Filed: Sep. 16, 2010

(65) Prior Publication Data

US 2011/0166463 A1 Jul. 7, 2011

Related U.S. Application Data

(62) Division of application No. 11/458,614, filed on Jul. 19, 2006, now Pat. No. 7,822,472.

(51) Int. Cl.
*A61B 5/04* (2006.01)
(52) U.S. Cl. .................................. 600/519; 600/520
(58) Field of Classification Search ........... 600/519–520
See application file for complete search history.

(56) References Cited

U.S. PATENT DOCUMENTS

| | | |
|---|---|---|
| 4,390,021 A | 6/1983 | Spurrell |
| 4,393,877 A | 7/1983 | Imran |
| 4,686,988 A | 8/1987 | Sholder |
| 4,708,142 A | 11/1987 | DeCote |
| 4,712,555 A | 12/1987 | Thornander |
| 4,729,376 A | 3/1988 | Decote |
| 4,788,980 A | 12/1988 | Mann |
| 4,790,528 A | 12/1988 | Nakao |
| 4,809,697 A | 3/1989 | Causey, III |
| 4,872,459 A | 10/1989 | Pless |
| 4,883,063 A | 11/1989 | Bernard |
| 4,938,228 A | 7/1990 | Righter |
| 4,940,952 A | 7/1990 | Kegasa |
| 4,944,298 A | 7/1990 | Sholder |
| 4,944,299 A | 7/1990 | Silvian |

(Continued)

FOREIGN PATENT DOCUMENTS

WO   WO 0064336 A1   11/2000

(Continued)

OTHER PUBLICATIONS

Non-Final Office Action mailed Feb. 23, 2009: Related U.S. Appl. No. 11/561,267.

(Continued)

*Primary Examiner* — Carl H Layno
*Assistant Examiner* — Luther Behringer
(74) *Attorney, Agent, or Firm* — Steven M. Mitchell

(57) ABSTRACT

A medical device detects certain patient activity based on a programmable activity threshold and determines the duration of detected activity. The activity threshold may be optimized by obtaining first and second duration measurements for at least one of a first activity session and second activity session. The first duration measurement is based on the activity threshold, while the second duration measurement is based on actual start and stop of the activity session. An adjustment of the activity threshold is suggested based on a correspondence between the first duration measurement and the second duration measurement of the first activity session, or a correspondence between the first duration measurement and the second duration measurement of the second activity session. One of the first and second activities is non-significant activity expected to be undetected by the device, while the other of the two activities is low-level activity expected to be detected by the device.

11 Claims, 21 Drawing Sheets

U.S. PATENT DOCUMENTS

| | | | |
|---|---|---|---|
| 4,969,465 A | 11/1990 | Pless |
| 4,969,467 A | 11/1990 | Callaghan |
| 4,971,058 A | 11/1990 | Pless |
| 5,065,759 A | 11/1991 | Begemann |
| 5,133,350 A | 7/1992 | Duffin |
| 5,144,949 A | 9/1992 | Olson |
| 5,284,491 A | 2/1994 | Sutton |
| 5,292,340 A | 3/1994 | Crosby |
| 5,327,900 A | 7/1994 | Mason |
| 5,350,410 A | 9/1994 | Klek |
| 5,365,934 A | 11/1994 | Leon |
| 5,549,649 A | 8/1996 | Florio |
| 5,720,769 A | 2/1998 | Van Oort |
| 5,738,104 A | 4/1998 | Lo |
| 6,045,513 A | 4/2000 | Stone |
| 6,081,747 A | 6/2000 | Levine |
| 6,102,874 A | 8/2000 | Stone |
| 6,190,324 B1 | 2/2001 | Kieval |
| 6,275,734 B1 | 8/2001 | McClure |
| 6,280,409 B1 | 8/2001 | Stone |
| 6,285,907 B1 | 9/2001 | Kramer |
| 6,361,503 B1 | 3/2002 | Starobin |
| 6,411,848 B2 | 6/2002 | Kramer |
| 6,438,408 B1 | 8/2002 | Mulligan |
| 6,477,420 B1 | 11/2002 | Struble |
| 6,501,988 B2 | 12/2002 | Kramer |
| 6,529,771 B1 | 3/2003 | Kieval |
| 6,539,249 B1 * | 3/2003 | Kadhiresan et al. ......... 600/510 |
| 6,645,153 B2 | 11/2003 | Kroll |
| 6,648,829 B2 | 11/2003 | Starobin |
| 6,648,830 B2 | 11/2003 | Starobin |
| 6,687,535 B2 | 2/2004 | Hautala |
| 6,904,313 B1 | 6/2005 | Snell |
| 6,961,615 B2 | 11/2005 | Kroll |
| 7,031,766 B1 | 4/2006 | Paris |
| 7,043,294 B1 | 5/2006 | Paris |
| 7,136,705 B1 * | 11/2006 | Park ............................... 607/27 |
| 7,142,918 B2 | 11/2006 | Stahmann |
| 7,149,568 B2 | 12/2006 | Amano |
| 7,192,401 B2 | 3/2007 | Saalasti |
| 7,330,752 B2 | 2/2008 | Kettunen |
| 2001/0016759 A1 | 8/2001 | Kramer |
| 2001/0029319 A1 | 10/2001 | Kazlausky |
| 2002/0082648 A1 | 6/2002 | Kramer |
| 2002/0082660 A1 | 6/2002 | Stahmann |
| 2002/0115938 A1 | 8/2002 | Hannula |
| 2002/0115939 A1 | 8/2002 | Mulligan |
| 2002/0151806 A1 | 10/2002 | Starobin |
| 2002/0151811 A1 | 10/2002 | Starobin |
| 2003/0069610 A1 | 4/2003 | Kramer |
| 2003/0074029 A1 | 4/2003 | Deno |
| 2003/0149370 A1 | 8/2003 | Starobin |
| 2003/0187479 A1 | 10/2003 | Thong |
| 2003/0208106 A1 | 11/2003 | Anderson |
| 2004/0152957 A1 | 8/2004 | Stivoric |
| 2005/0065443 A1 | 3/2005 | Ternes |
| 2005/0187585 A1 | 8/2005 | Mussig |
| 2005/0256414 A1 | 11/2005 | Kettunen |
| 2006/0229163 A1 | 10/2006 | Waters |

FOREIGN PATENT DOCUMENTS

| | | |
|---|---|---|
| WO | WO 0071202 A1 | 11/2000 |
| WO | WO 02051496 A2 | 7/2002 |
| WO | WO 02051496 A3 | 7/2002 |
| WO | WO 02053026 A2 | 7/2002 |
| WO | WO 02053026 A3 | 7/2002 |
| WO | WO 02053228 A1 | 7/2002 |
| WO | WO 03057032 A1 | 7/2003 |
| WO | WO 03057033 A1 | 7/2003 |

OTHER PUBLICATIONS

Final Office Action mailed Aug. 13, 2009: Related U.S. Appl. No. 11/561,267.

Non-Final Office Action mailed Sep. 29, 2005: Related U.S. Appl. No. 10/828,897.

Notice of Allowance mailed Jan. 20, 2006: Related U.S. Appl. No. 10/828,897.

Non-Final Office Action mailed Apr. 1, 2009: Related U.S. Appl. No. 11/405,129.

Final Office Action mailed Oct. 7, 2009: Related U.S. Appl. No. 11/405,129.

Notice of Allowance mailed Jan. 15, 2010: Related U.S. Appl. No. 11/405,129.

Non-Final Office Action mailed Oct. 16, 2009: Related U.S. Appl. No. 11/458,614.

Final Office Action mailed Mar. 25, 2010: Related U.S. Appl. No. 11/458,614.

Final Office Action mailed Jun. 14, 2010: Related U.S. Appl. No. 11/458,614.

Notice of Allowance mailed Aug. 20, 2010: Related U.S. Appl. No. 11/458,614.

Non-Final Office Action mailed Oct. 13, 2005: Related U.S. Appl. No. 10/828,883.

Notice of Allowance mailed Jan. 10, 2006: Related U.S. Appl. No. 10/828,883.

Non-Final Office Action mailed Jul. 10, 2009: Related U.S. Appl. No. 11/351,859.

Non-Final Office Action mailed Jan. 25, 2010: Related U.S. Appl. No. 11/351,859.

Final Office Action mailed Jul. 7, 2010: Related U.S. Appl. No. 11/351,859.

Non-Final Office Action mailed Jun. 26, 2009: Related U.S. Appl. No. 11/351,401.

Notice of Allowance mailed Dec. 15, 2009: Related U.S. Appl. No. 11/351,401.

* cited by examiner

METHODS AND SYSTEMS FOR OPTIMIZING EXERCISE COMPLIANCE DIAGNOSTIC PARAMETERS

PRIORITY CLAIM

This application is a Divisional of U.S. patent application Ser. No. 11/458,614, Jul. 19, 2006, now issued as U.S. Pat. No. 7,822,472 2006, titled "Methods And Systems for Optimizing Exercise Compliance Diagnostic Parameters."

FIELD OF THE INVENTION

The present invention relates generally to exercise compliance diagnostics and more particularly to systems and methods for optimizing parameters used in such diagnostics.

BACKGROUND

An implantable cardiac device is a medical device that is implanted in a patient to monitor electrical activity of the heart and to deliver appropriate electrical and/or drug therapy, as required. Implantable cardiac devices include, for example, pacemakers, cardioverters and defibrillators. The term "implantable cardioverter defibrillator" or simply "ICD" is used herein to refer to any implantable cardiac device. An ICD employs a battery to power its internal circuitry and to generate electrical therapy. The electrical therapy can include, for example, pacing pulses, cardioverting pulses and/or defibrillator shock pulses.

Heart failure is a growing medical challenge. In clinical practice today, most patients are managed effectively through pharmacological therapy such as beta-blockers, ACE inhibitors, and diuretics. If a patient's condition worsens, treatment may become more aggressive to include biventricular pacing and other implantable cardiac device therapy. Along with providing the primary objectives in the treatment of heart failure of improving symptoms, increasing the quality of life, and slowing disease progression, devices need to provide heart failure physicians with diagnostic parameters to monitor the patient's progress.

Currently, medical history and physical examination are the most important tools that a physician uses to determine and mark the progress of a heart failure patient. This involves much of the physician's time with the patient, as this may lead to the primary management program for the patient.

Included in most management programs is an exercise routine. It has been written extensively that adherence to exercise is a priority in improving or in maintaining good heath. Exercise diagnostics may help clinicians assess the compliance of the management programs prescribed to their patients, and possibly assist the patient in meeting those goals.

During exercise, the heart rate is a parameter or indicator of the amount of work that was required to provide blood and oxygen to the body. The maximum heart rate for a level of exercise corresponds to the conditioning of the heart. Other parameters, such as heart rate intensity, percent oxygen consumption (% $VO_2$) reserve, metabolic equivalents (METS), and workload also provide data that is indicative of heart conditioning.

Heart rate recovery after exercise is evaluated as a clinical marker of good vagal activity and cardiac health. As the heart rate increases due to a reduction in vagal tone, the heart rate also decreases with a reactivation of vagal activity. A delayed response to the decreasing heart rate may be a good prognostic marker of overall mortality (Cole, C. et al., NEJM 341:18, 1351-1357 (1999)) and cardiac health. Cole suggests that a reduction of only 12 beats per minute after one minute from peak exercise has been shown to be an abnormal value.

As previously mentioned, adherence to an exercise routine is a priority in managing heart failure progression; therefore, it is critical that a physician monitor significant patient activity, i.e., the time the patient is moving around in a potential exercise-like manner, and patient exercise, i.e., the time the patient is continuously moving around in an exercise-like manner. One method of monitoring patient activity and exercise relies on subjective and often inaccurate reporting of exercise duration and workload/intensity level by the patient.

Other more objective methods of monitoring patient activity and exercise rely on algorithms that monitor for significant patient activity by comparing patient activity data obtained through, physiological sensors, against an activity threshold. Such algorithms may employ an automated process for initially setting the activity threshold using patient activity data collected over a period of time, after implant of the device. For some people, however, the initial activity threshold setting may overtime, result in system performance that is less than optimal. For example, an over-sensitive threshold value may cause the algorithm to consider a patient's daily activity such as office work, reading and talking as significant activity. Conversely, an under-sensitive threshold value may cause the algorithm to exclude low-level, significant activity, e.g., light walking, from its exercise diagnostic routine. Therefore, periodic verification, recalibration or optimization of the activity threshold is desirable to ensure accurate detection of, and distinction between, low-level, significant activity and non-significant activity.

SUMMARY

Briefly, and in general terms the invention is directed to patient-associated medical devices that are operative to detect certain patient activity based on a programmable activity threshold and to determine the duration of detected activity. The activity threshold may be optimized by obtaining first and second duration measurements for at least one of a first activity session and second activity session. The first duration measurement is based on the activity threshold, while the second duration measurement is based on actual start and stop of the activity session. An adjustment of the activity threshold is suggested based on at least one of a correspondence between the first duration measurement and the second duration measurement of the first activity session, and a correspondence between the first duration measurement and the second duration measurement of the second activity session. One of the first and second activities is non-significant activity expected to be undetected by the device, while the other of the two activities is low-level activity expected to be detected by the device.

These and other aspects and advantages of the invention will become apparent from the following detailed description and the accompanying drawings which illustrate by way of example the features of the invention.

BRIEF DESCRIPTION OF THE DRAWINGS

FIG. 13B is a graph of correlation values as a function of time corresponding to the same patient activity, on a Stairmaster shown in FIG. 12a;

DETAILED DESCRIPTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designations will be used to refer to like parts or elements throughout.

It will be apparent to one of skill in the art that the present invention, as described below, may be implemented in many different embodiments of hardware, software, firmware, and/or the entities illustrated in the figures. Any actual software and/or hardware described herein is not meant to limit the scope of the present invention. Thus, the structure, operation and behavior of the present invention will be described with the understanding that many modifications and variations of the embodiments are possible, given the level of detail presented herein.

Figure 1A:
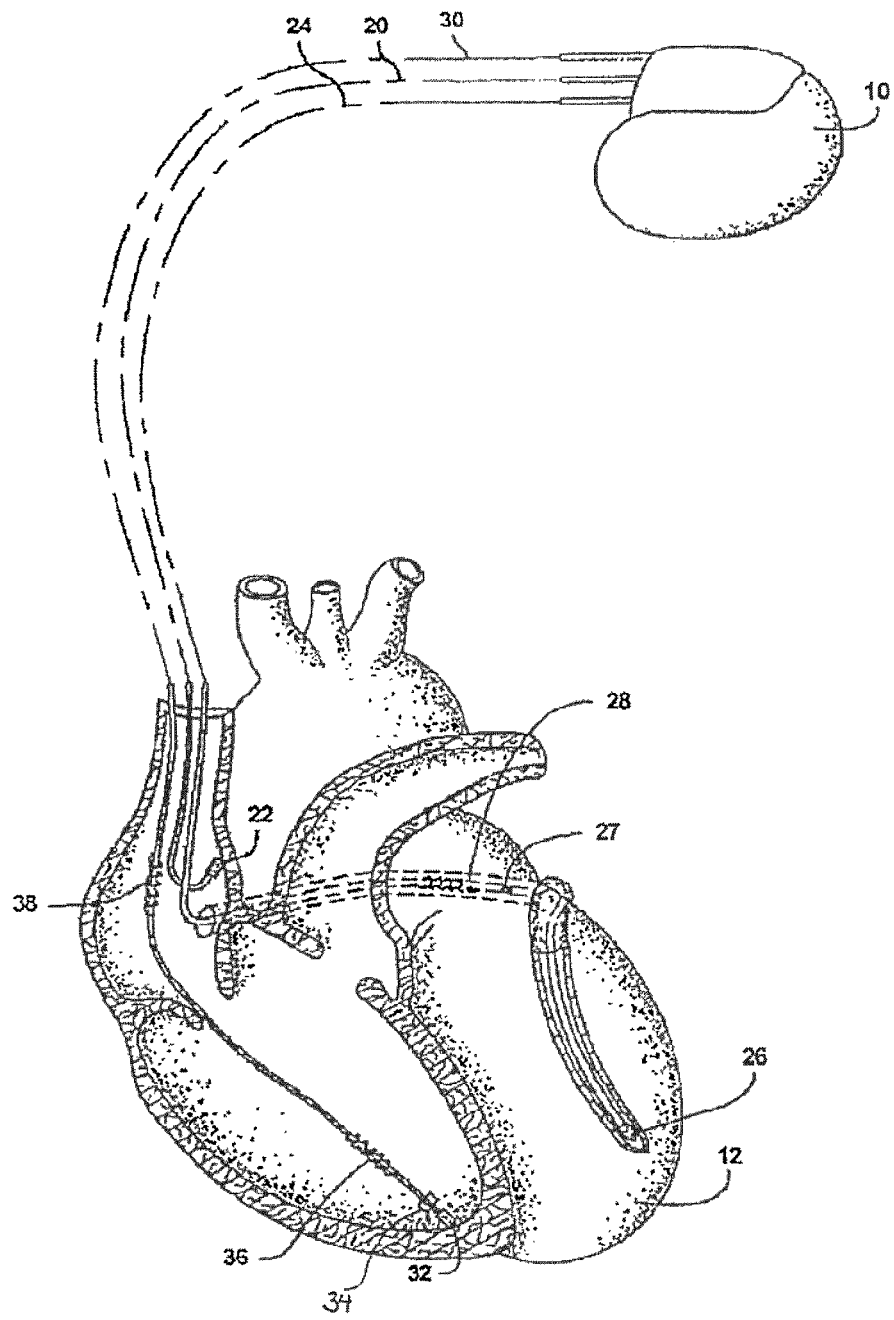
FIG. 1A is a simplified diagram illustrating an exemplary ICD in electrical communication with at least three leads implanted into a patient's heart for delivering multi-chamber stimulation and shock therapy.
Figure 1B:
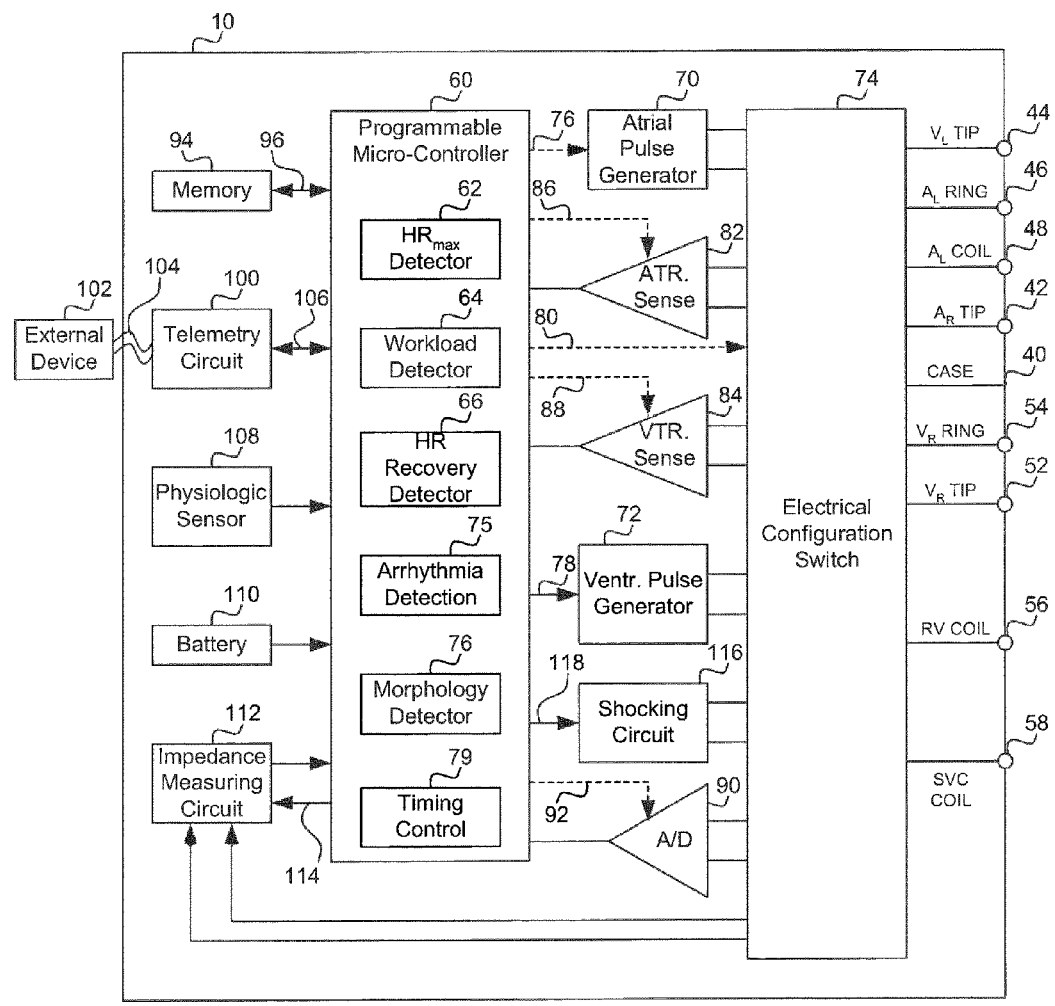
FIG. 1B is a functional block diagram of an exemplary ICD, which can provide cardioversion, defibrillation and pacing stimulation in four chambers of a heart.

Before describing the invention in detail, it is helpful to describe an example environment in which the invention may be, implemented. The present invention is particularly useful in the environment of an implantable cardiac device. Implantable cardiac devices include, for example, pacemakers, cardioverter-defibrillators, and hemodynamic monitors. The term "implantable cardioverter defibrillator" or simply "ICD" is used herein to refer to any implantable cardiac device or implantable cardioverter-defibrillator. FIGS. 1A and 1B illustrate such an environment.

As shown in FIG. 1A, there is an exemplary ICD 10 in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36; and an SVC coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the superior vena cava. Accordingly, right ventricular lead 30 is capable of receiving cardiac signals and delivering stimulation in the form of pacing and shock therapy to the right ventricle.

FIG. 1B shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 1B, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

At the core of ICD 10 is a programmable microcontroller 60 which controls the various modes of stimulation therapy. As is well known in the art, microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art. In specific embodiments of the present invention, microcontroller 60 performs some or all of the steps associated with the exercise diagnostics in accordance with the present invention.

Representative types of control circuitry that may be used with the invention include the microprocessor-based control system of U.S. Pat. No. 4,940,052 (Mann et al.) and the state-machines of U.S. Pat. No. 4,712,555 (Thornander et al.) and U.S. Pat. No. 4,944,298 (Sholder). For a more detailed description of the various timing intervals used within the ICDs and their inter-relationship, see U.S. Pat. No. 4,788,980 (Mann et al.). The '052, '555, '298 and '980 patents are incorporated herein by reference.

As shown in FIG. 1B, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70, 72, may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses.

Microcontroller 60 further includes timing control circuitry 79 which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic sensitivity control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 84.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detection circuitry 75 and morphology detection circuitry 76 to recognize and classify arrhythmia so that appropriate therapy can be delivered.

Cardiac signals are also applied to the inputs of an analog-to-digital (ND) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Advantageously, data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (DeCote, Jr.); U.S. Pat. No. 4,708,142 (DeCote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. The type of capture detection system used is not critical to the present invention.

Microcontroller 60 also contains maximum observed heart rate ($HR_{max}$) detector 62, workload detector 64, and/or a heart rate recovery detector 66. The operation of the $HR_{max}$ detector, workload detector, and heart rate recovery detector are discussed below in connection with the methods of the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of ICD 10 may be non-invasively programmed into memory 94 through a telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through an established communication link 104.

For examples of such devices, see U.S. Pat. No. 4,809,697, entitled "Interactive Programming and Diagnostic System for use with Implantable Pacemaker" (Causey, Ill. et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

In one embodiment, ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.) in accordance with the embodiments of the present invention. Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream). As discussed below, sensor 108 can also be used to measure activity level.

ICD 10 additionally includes a battery 110 which provides operating power to all of the circuits shown in FIG. 1B. For ICD 10, which employs shocking therapy, battery 110 must be capable of operating at low current drains for long periods of time, and then be capable of providing high-current pulses (for capacitor charging) when the patient requires a shock pulse. Battery 110 must also have a predictable discharge characteristic so that elective replacement time can be detected. Accordingly, ICD 10 preferably employs lithium/silver vanadium oxide batteries, as is true for most (if not all) current devices.

ICD 10 further includes a magnet detection circuitry (not shown), coupled to microcontroller 60. It is the purpose of the magnet detection circuitry to detect when a magnet is placed over ICD 10, which magnet may be used by a clinician to perform various test functions of ICD 10 and/or to signal microcontroller 60 that the external programmer 102 is in place to receive or transmit data to microcontroller 60 through telemetry circuit 100.

As further shown in FIG. 1B, ICD 10 is shown as having an impedance measuring circuit 112 which is enabled by microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 116 by way of a control signal 118. The shocking circuit 116 generates shocking pulses of low (up to 0.5 Joules), moderate (0.5-10 Joules), or high energy (11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognized), and pertaining exclusively to the treatment of fibrillation. Accordingly, microcontroller 60 is capable of controlling the synchronous or asynchronous delivery of the shocking pulses.

With the description of an example environment, such as an ICD, in mind, features of the present invention are described in more detail below.

Figure 2:
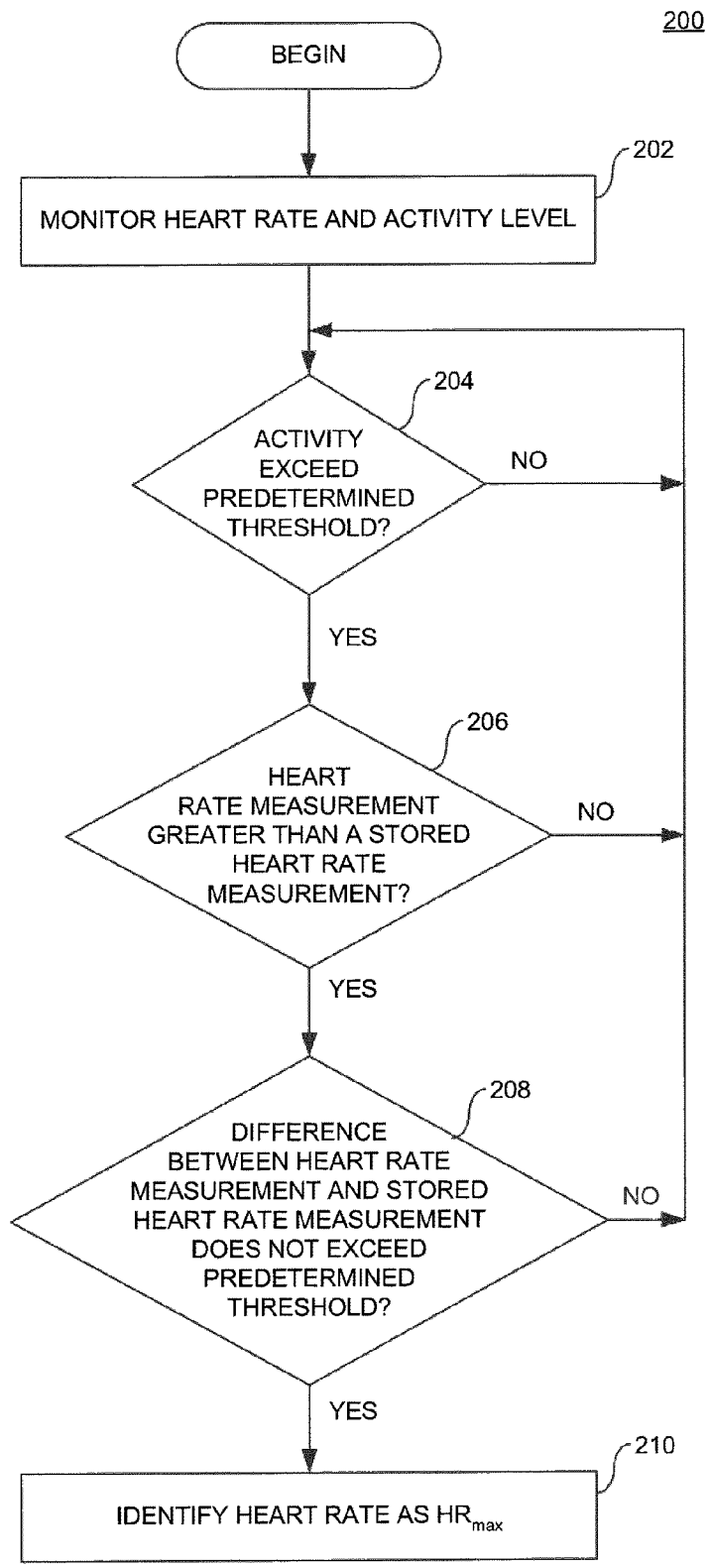
FIG. 2 is a flow chart illustrating an embodiment of a method for determining an observed maximum heart rate of a patient during exercise.

A method 200 of determining a maximum observed heart rate ($HR_{max}$) of a patient during exercise is illustrated in FIG. 2. According to an embodiment, the method 200 begins at step 202, in which the heart rate and activity level of the patient are monitored. The heart rate and activity level of the patient may be continuously monitored during the method 200.

The patient's heart rate may be determined by any suitable method. Many variations on how to determine heart rate are known to those of ordinary skill in the art, and any of these of reasonable accuracy may be used. Heart rate can be determined by measurement of an R-R interval cycle length (or P-P), which is the inverse of heart rate. As used herein, the heart rate (in beats per minute) can be seen as the inverse to cycle length, determined by 60,000 divided by the cycle length (in milliseconds).

Heart rate measurements can be produced based upon the monitored heart rate. Such heart rate measurements include but are not limited to heart rate and heart rate intensity.

The activity level of the patient may also be determined by any suitable method. For example, the activity level may be determined by an accelerometer, piezoelectric crystal, minute ventilation, photoplethysmography, or a derivative thereof, such as the sensor indicated rate. In one embodiment, activity level is determined using physiologic sensor 108. In this embodiment, sensor 108 is an accelerometer, a piezoelectric crystal, an impedance sensor, or a photoplethysmography sensor.

In step 204, the measured activity level is compared with a predetermined activity threshold to determine whether the activity level exceeds the threshold. The predetermined activity threshold can be a value that corresponds to a certain level of exercise. It should be appreciated that the activity threshold value can be tailored for a specific patient's condition. Illustratively, an activity threshold value which correlates with walking or some other low level of exercise may be, for example, 50 milligravities as measured by an accelerometer.

It should be understood that in the context of the present invention, when comparing a measurement to a threshold, the terms "exceeds" or "is greater than" encompass instances when the measurement is equal to the threshold value. Similarly, it should be understood that the terms "falls below" or "is less than" a threshold value encompass instances when the measurement is equal to the threshold value. A person skilled in the relevant art will recognize that selection of a threshold value, and how to treat the condition of equality between the threshold and the measurement are design choices.

The activity level can be compared with an activity threshold at various time intervals or periodically to determine whether the activity level exceeds the predetermined threshold. The particular selected time interval for monitoring is not critical. In one embodiment of the invention, the activity level is monitored and compared with the activity threshold at time intervals of 30 seconds (i.e., every 30 seconds).

If the patient activity level exceeds the predetermined activity threshold, then the method proceeds to step 206. Illustratively, if 50 milligravities activity is a threshold that correlates well with walking or some low level of exercise and the implantable medical device is programmed at this threshold, then if the measured activity level exceeds 50 milligravities, the method proceeds to step 206.

Steps 206 and 208 can be performed when the patient activity level exceeds the predetermined activity threshold for a predetermined period of time. This predetermined period of time can be an amount that one skilled in the art would understand to be sufficient for the heart to react to the exercise by the patient (which can be indicated by e.g., the activity level exceeding the predetermined activity threshold). Illustratively, the predetermined period of time may be 10 seconds to five minutes, preferably about two to three minutes, more preferably about two minutes.

In step 206, a heart rate measurement is compared with a stored heart rate measurement. The stored heart rate measurement can be, for example, a heart rate measurement previously obtained during exercise, including a previously determined $HR_{max}$ during exercise. Prior to first occurrence of the method, the stored heart rate measurement can be set to a predetermined default value. If the heart rate measurement exceeds the previously stored heart rate measurement, then the method proceeds to step 208. Otherwise, step 204 is repeated. That is, the method continues to monitor heart rate and activity level and produce heart rate measurements.

In step 208, the difference between the heart rate measurement and the stored heart rate measurement is compared to a predetermined threshold. The predetermined threshold difference may be selected to correspond to a value above which may be indicative of noise, PACs, PVCs, and/or arrhythmias. If the difference between the heart rate measurement and the stored heart rate measurement exceeds the threshold difference, the measured heart rate is not considered to be a $HR_{max}$. The threshold may even be step-size units, so as to show a gradual (physiologic) increase.

In accordance with one embodiment, step 208 is not performed. However, this embodiment is less preferred, as the resulting $HR_{max}$ could be inaccurate due to noise and/or premature heartbeats.

It should be understood that the order of comparison steps 206 and 208 is not limited to that depicted in the figure and may be performed in reverse order or conducted simultaneously.

If, in step 206, the heart rate measurement is greater than the stored heart rate measurement and, in step 208, the difference between the heart rate measurement and the stored heart rate measurement does not exceed a predetermined threshold, then the heart rate associated with the heart rate measurement may be identified as a maximum observed heart rate ($HR_{max}$). In other words, a heart rate can be identified as a $HR_{max}$ when the comparison steps 204, 206, and 208 are met.

The maximum observed heart rate may be recorded as a stored value, and the method 200 repeated, using the $HR_{max}$ as a new stored heart rate measurement. The $HR_{max}$ determination may be continued until activity level and/or heart rate is indicative of a slow-down of exercise.

Based on the $HR_{max}$ obtained, further values may be obtained that are indicative of heart conditioning. These values include heart rate intensity, percent oxygen consumption (%$VO_2$) reserve, metabolic equivalents (METS), percentage METS, workload, and absolute oxygen uptake.

For example, heart rate intensity (also known as percent heart rate reserve, heart rate capacity, target heart rate, or % HRR) may be calculated by dividing $HR_{max}$ by the predicted age compensated maximum heart rate as follows:

$$\% \ HRR = \frac{HR_{max} - \text{resting } HR}{\text{Age Compensated Maximum } HR - \text{resting } HR} \times 100$$

In the equation indicated above, resting heart rate of the patient may be obtained by any suitable method including, for example, a heart rate measurement taken when the activity level of the patient is sufficiently low to be considered inactive. The age compensated maximum heart rate can be calculated by the formula: (220-age).

With % HRR, it is also possible to calculate %$VO_2$ reserve. Swain et al. have shown a close correlation between % HRR and %$VO_2$ reserve ("Heart rate reserve is equivalent to % $VO_2$ reserve, not % $VO_{2max}$," Med. Sci. Sports Exercise 29:410-414 (1997)).

%$VO_2$ reserve is an intensity scale or index that describes the percentage of oxygen intake used during exercise. The value between % $VO_2$ reserve and 100% is the amount of oxygen intake reserves available. This value may be obtained by the following equation (Swain et al., Target HR for the development of CV fitness, Medicine & Science in Sports & Exercise 26(1):112-116):

%$VO_2$ reserve=(%$HRR$-37)/0.64 where % HRR is calculated as described above.

Workload is measure of intensity times duration, and may be seen by the following equation:

Workload=Intensity*Duration where Intensity is $VO_{2observed}$, but may also be seen as an index such as heart rate intensity (% HRR) or % $VO_2$ reserve as discussed above, and Duration is the time during exercise when activity is above a predetermined threshold. It is possible to use in the calculation of work only % HRR values above a predetermined threshold (e.g., >40%), reflective of at least moderate exercise. An additional method involves multiplying the mean % HRR above the predetermined threshold by the total duration.

A primary expression of intensity throughout the clinical community is metabolic equivalents (METS). METS is a measure of Intensity or functional capacity. One (1) MET is equivalent to the amount of energy used at rest (oxygen uptake of 3.5 ml/(kg*min)), or the resting $VO_2$.

1 $MET$=3.5 mL/(kg*min)=$VO_2$ resting

METS are linked to heart rate intensity. See, Strath et al., "Evaluation of Heart Rate as a Method for Accessing Moderate Intensity Physical Activity," Med. & Sci. in Sports & Exerc., 465-470 (2000).

One method for determining METS has been described by Wilkoff, B. L., et al. ("A Mathematical Model of the Cardiac Chronotropic Response to Exercise," J. Electrophysiol. 3:176-180 (1989)), in which a mathematical model was developed describing the relationship of percentage metabolic equivalents (% METS) to heart rate intensity using the CAEP and Bruce exercise protocols. They found that the relationship was linear, with a slope of approximately 1 (1.06), by the equation:

% METS=1.06*(% HRR)-4.87

Observed METS during exercise can be obtained through the following equation:

$$\% \ METS = \frac{(METS_{observed} - METS_{rest})}{(METS_{max} - METS_{rest})} * 100\%$$

with $METS_{rest} = 1$

The value for $METS_{max}$ to be used in the above equation may be obtained as follows:

Predicted $METS_{max}$=16.6-0.16(age)

This predicted $METS_{max}$ value is an approximation, as it was obtained by a nomogram of sedentary men who participated in the USAir Force School of Aerospace Medicine Protocol, and who did not have a history of CHF. See Morris et al., "Nomogram Based on Metabolic Equivalents and Age for Assessing Aerobic Exercise Capacity in Men," J. Am. Coll. Cardiol. 22:175-182 (1993). However, if this approximation is used as a best fit method for maximal METS expected for each patient, $METS_{observed}$ can thus be calculated as:

$METS_{observed}$=(%$METS$/100)*((16.6-0.16*(age))-1)+1

METS can also be determined by the following method by alternatively solving for %$VO_2$ reserve. %$VO_2$ reserve can be calculated by the following equation:

$$\% \ VO_2 \ \text{reserve} = \frac{(VO_{2observed} - VO_{2rest})}{(VO_{2max} - VO_{2rest})} * 100\%$$

with $VO_{2rest} = 1$ where $VO_{2max}$ can be obtained from the non-exercise prediction equation of Jackson et al., "Prediction of functional aerobic capacity without exercise testing," Med. Sci. Sports & Exerc J. 22:863-870 (1990) by:

$VO_2$=50.513+1.589*(activity scale[0 . . . 7])-0.289*(age)-0.552*(% fat)+5.863*(F=0, M=1).

Or, for those times when % fat may be difficult to obtain, the following equation by Jackson et al. allows for use of Body Mass Index (BMI):

$VO_{2max}$=56.363+1.921*(activity scale[0 . . . 7])-0.381*(age)-0.754*(BMI)+10.987*(F=0, M=1)

In the above two equations for $VO_{2max}$, activity scale can be related to % HRR as a level of activity, % fat or BMI is either calculated as an average over the population or a value to be uploaded to the ICD, and F and M designate female and male, respectively.

When $VO_{2max}$ is plugged back into the % $VO_2$ equation, $VO_{2observed}$ can be obtained (units of mL/[kg*min]). $METS_{observed}$ can be obtained by dividing $VO_{2observed}$ by 3.5.

Another way to determine $VO_{2max}$ is by the Astrand single-stage submaximal method, with the following equation:

$$VO_{2max} = VO_{2observed} * [(\text{Age compensated max. } HR-K)/(HR_{observed}-K)]$$

where K=63 for men and 73 for women. (Astrand, P. O., and Rodah, K., *Textbook of Work Physiology*, 3$^{rd}$ Ed. New York: McGraw-Hill, 1986, p. 318-325 and 340-358.)

Once $METS_{observed}$ has been calculated, it is possible to get the following values:

Relative Oxygen consumption (ml/(kg*min)): $METS/3.5$

Absolute Oxygen Uptake (L/min): $VO_{2max}$*Weight

Calories (kcal): 1L $O_2$=5 kcal: $(VO_{2max}*\text{duration})/5$

Joules: 1 Kcal=4186 J

If the value for METS has a large standard deviation over the above equations, it can be further worked into a descriptive intensity scale (light, moderate, vigorous) as defined by Ainsworth B E et al., Compendium of physical activities: an update of activity codes and MET intensities, *Med Sci. Sports Exerc.*; 9:S498-S516 (2000)) where these can be defined by:

$METS_{60\% \text{ max cardiorespiratory capacity}} = [0.6*(60-0.55*(\text{age})]/3.5$ for men, and $METS_{60\% \text{ max cardiorespiratory capacity}} = [0.6*(48-0.37*(\text{age})]/3.5$ for women with 60% max cardiorespiratory capacity (MCC) considered vigorous. Therefore, light intensity would be, for example, between 20-40%, and moderate activity would be, for example, between 40-60%.

Figure 3A:
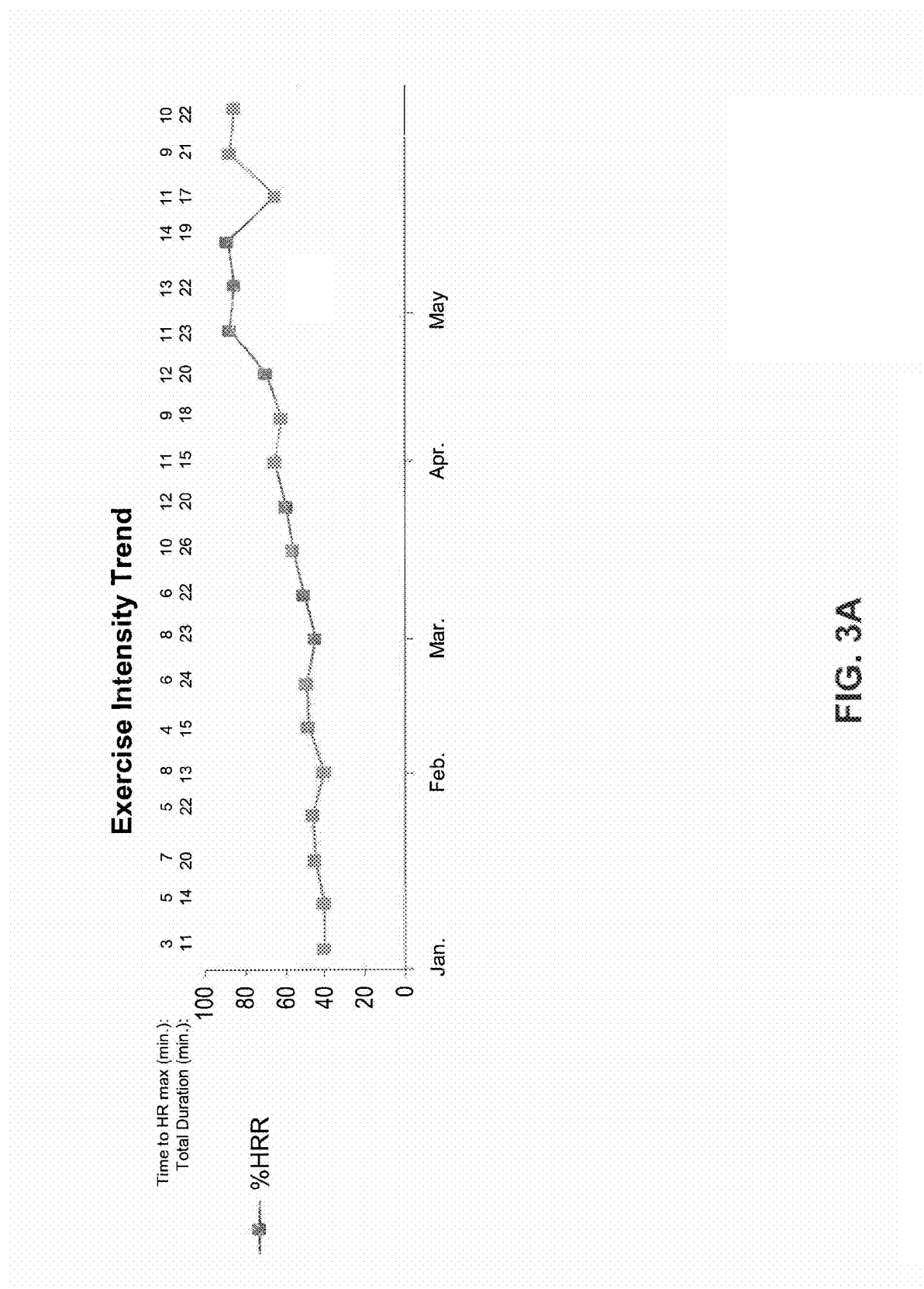
FIGS. 3A-3D illustrate representations of sample exercise diagnostic results.
Figure 3B:
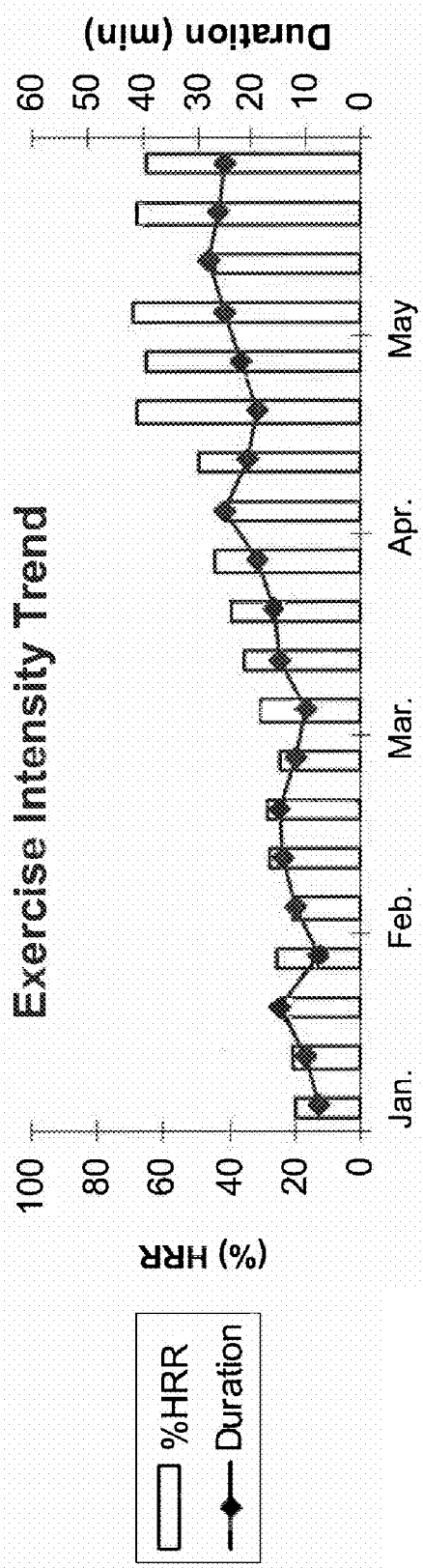
Figure 3C:
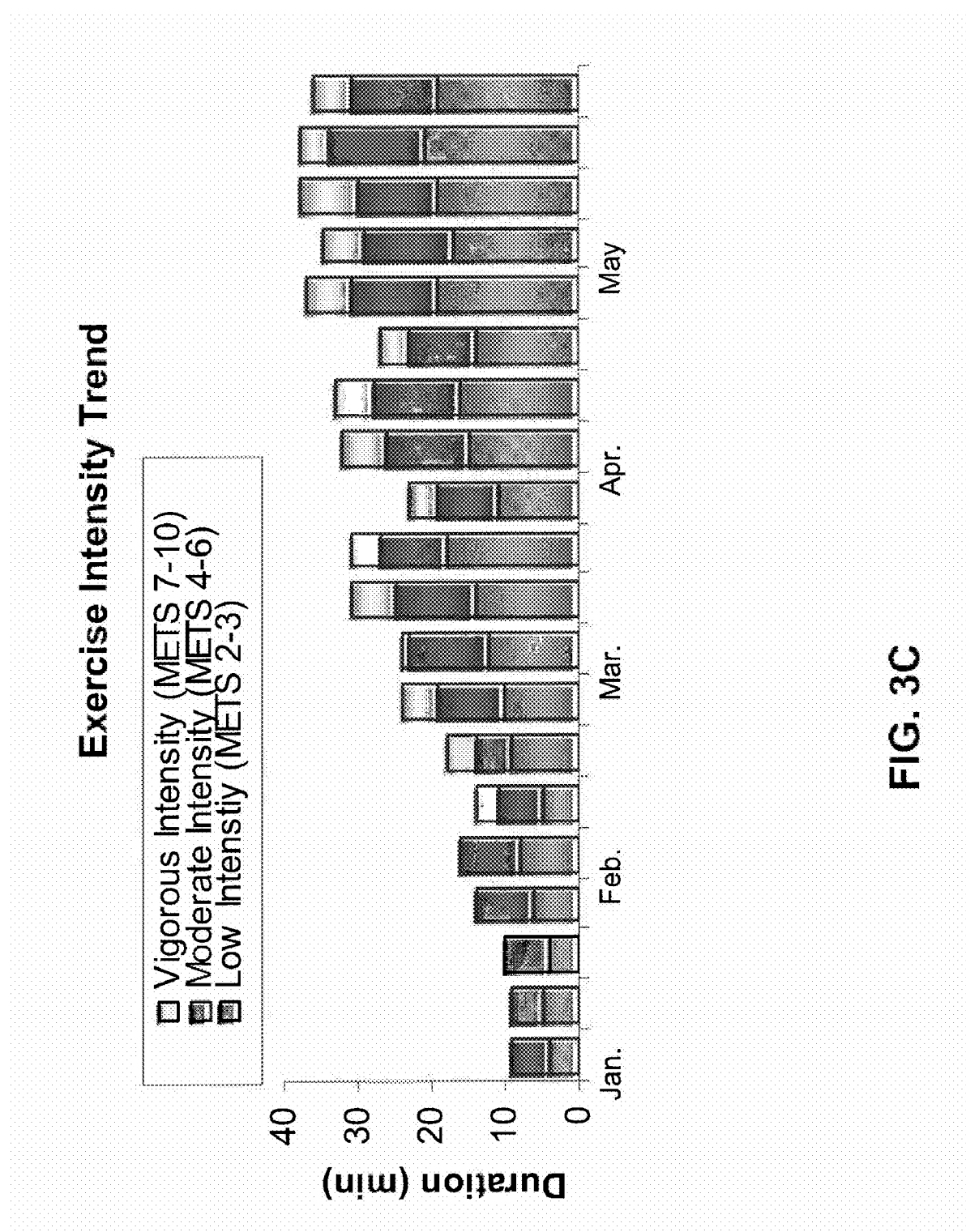
Figure 3D:
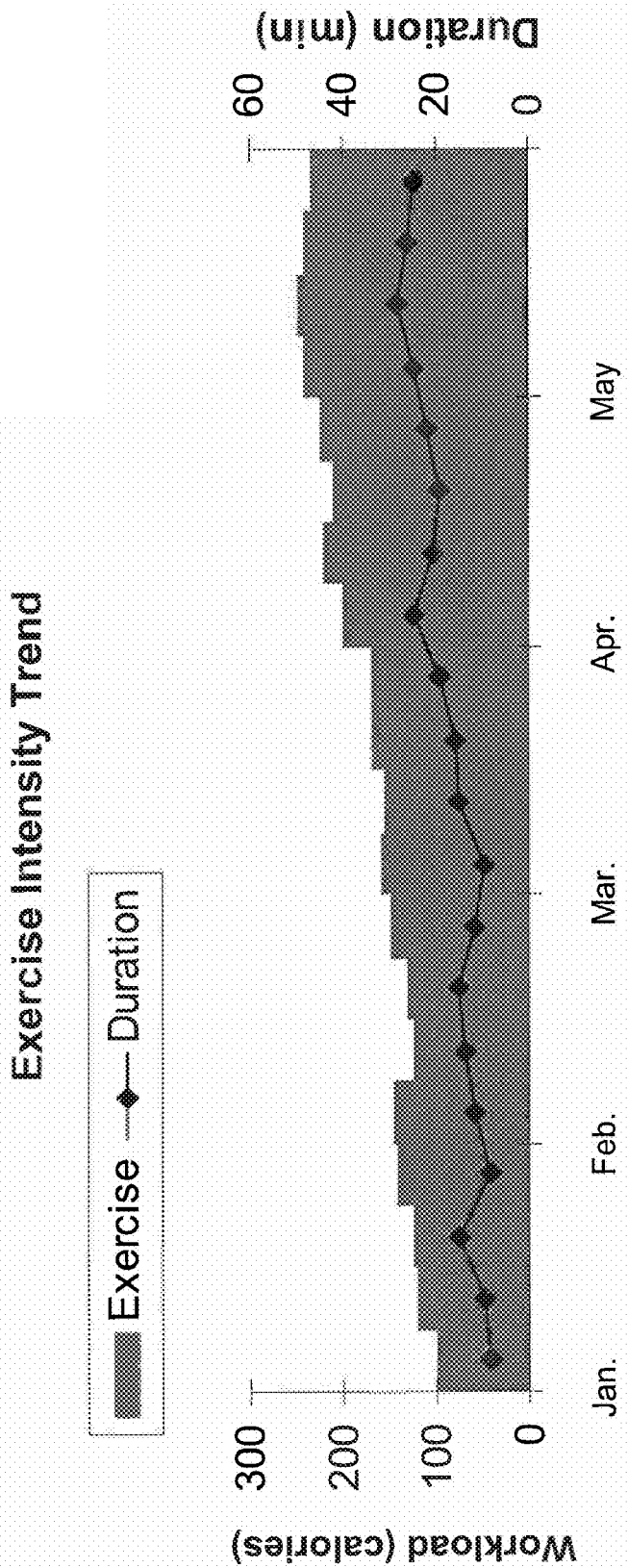

FIGS. 3A to 3D illustrate how exercise data, such as exercise intensities may be displayed. The data illustrated in these Figures are prophetic. In FIG. 3A, measured heart rate intensity (% HRR) data is displayed as a function of time in the graph. The table above the chart illustrates the corresponding time to $HR_{max}$ and the total duration of $HR_{max}$. In FIG. 3B, measured heart rate intensity and total duration of $HR_{max}$ are illustrated on one graph. In FIG. 3C, measured exercise intensity in the units of METS is illustrated, with corresponding amounts of vigorous, moderate, and low intensities, and the duration of each amount. In FIG. 3D, measured workload is illustrated, with corresponding duration of the workload. Each data point illustrated on the table and graphs of FIGS. 3A-3D represent an average over one week.

As is illustrated from FIGS. 3A-3D, the invention also encompasses determining the time period associated with exercise intensities. For example, the time to and duration of $HR_{max}$ and workload can be determined.

The above-described method 200 for determining the maximum observed heart rate of a patient during exercise may be implemented by hardware, software, or firmware of a pacing system, such as the ICD described earlier with reference to FIGS. 1A and 1B, with particular reference to $HR_{max}$ detector 62.

In another embodiment, a method for determining exercise diagnostics, such as workload, heart rate intensity, percent oxygen consumption (% $VO_2$) reserve, metabolic equivalents (METS), percentage METS, and absolute oxygen uptake may be obtained without obtaining $HR_{max}$. This method includes monitoring a changing heart rate of a patient and producing heart rate measurements, monitoring activity level, and determining an exercise diagnostic, such as workload of the patient using at least one heart rate measurement when the activity level exceeds an activity threshold.

Figure 4:
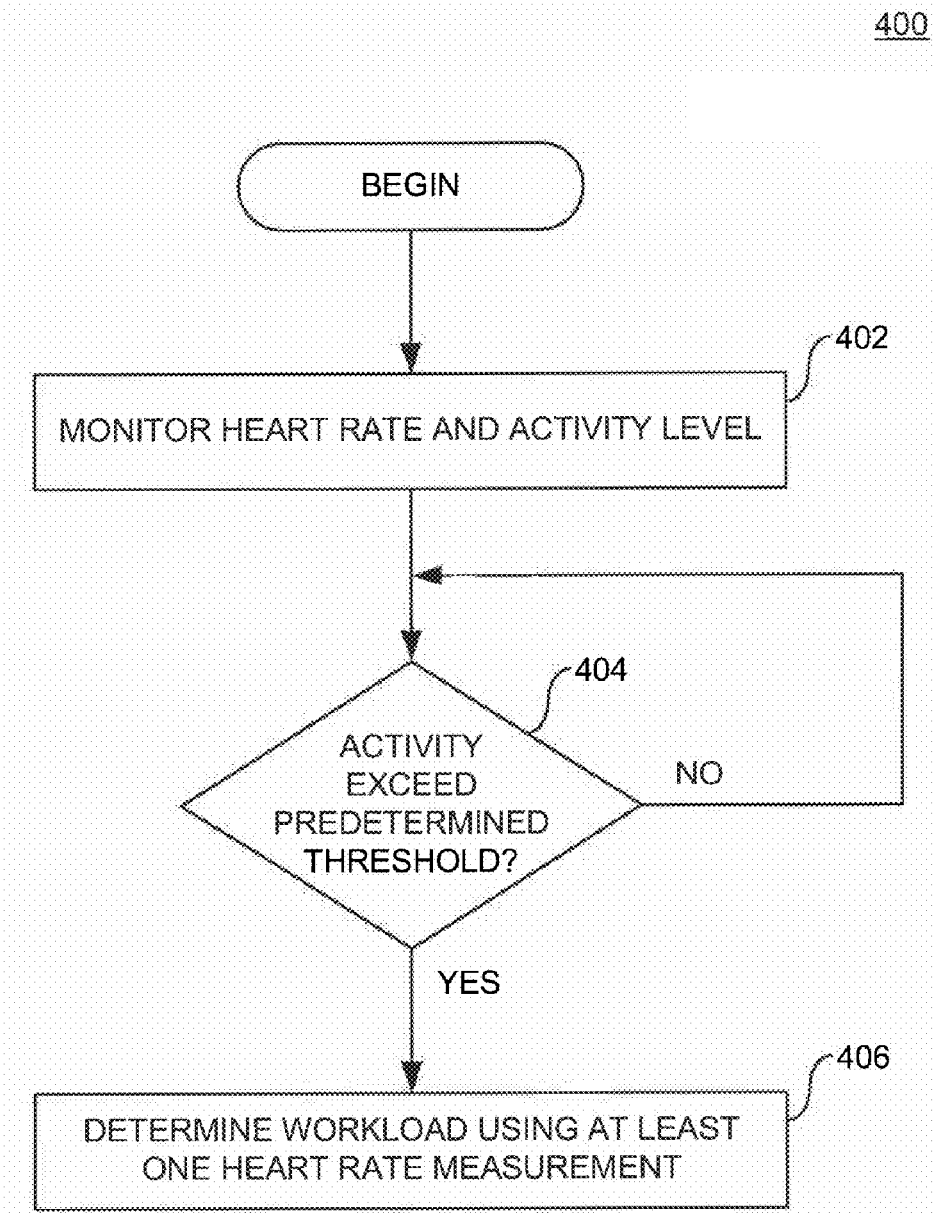
FIG. 4 is a flow chart illustrating an embodiment of a method for determining an exercise diagnostic such as work of a patient during exercise.

A method 400 of determining workload of a patient during exercise is illustrated in FIG. 4. According to an embodiment, the method 400 begins at step 402, in which the heart rate and activity level of the patient is monitored. The heart rate and activity level of the patient may be continuously monitored during the method 400.

As discussed above in conjunction with the method for determining $HR_{max}$, the patient's heart rate and activity level may be determined by any suitable method, and heart rate measurements can be generated based upon the monitored heart rate. In embodiments, the heart rate measurements include heart rate intensity.

In step 404, the measured activity level is compared with a predetermined activity threshold to determine whether the activity level exceeds the threshold. As discussed above, the predetermined activity threshold can be a value that corresponds to a certain level of exercise and can be tailored for a specific patient's condition.

The activity level can be compared with an activity threshold at various time intervals to determine whether the activity level exceeds the predetermined threshold for a predetermined period of time. The time interval or frequency of comparing the activity level with the activity threshold is not critical to the invention. In an embodiment, the activity level is monitored and compared with the activity threshold at time intervals of 30 seconds.

If it is determined in step 404 that the patient activity level exceeds a predetermined activity threshold, then step 406 is performed. As discussed above in conjunction with determining $HR_{max}$, step 406 can be performed when the patient activity level exceeds the predetermined activity threshold for at least a predetermined period of time. This predetermined period of time may correlate to the amount of time for the heart to react to the exercise by the patient. Illustratively, the predetermined period of time may be 10 seconds to five minutes, preferably about two to three minutes, more preferably about two minutes.

In step 406, workload of the patient is determined using at least one heart rate measurement. Preferably, a heart rate measurement that is used to determine work of the patient during the exercise is heart rate intensity.

Specifically, workload of a patient during exercise can be determined by the summation of intensities over time over the full time of exercise (i.e., for the entire period that the activity level exceeds the predetermined threshold), where intensities are calculated from, the previous equations discussed to obtain $VO_{2observed}$. Alternately, as discussed above, workload may be described as a unitless index by multiplying intensities such as % HRR or % $VO_2$ reserve and time Illustratively, after the activity level exceeds an activity threshold, work values can be calculated (Intensity*Duration) for each datapoint until the cessation of exercise (i.e., when the activity level no longer exceeds the predetermined threshold). The determination of work of the patient during the exercise can also be represented by the following formula:

$$\Sigma \text{Intensity}(x)*(\text{Time}(x)-\text{Time}(x-1))$$

where x=0:n.

Based on the workload value obtained above, other exercise diagnostics, such as heart rate intensity, percent oxygen consumption (% $VO_2$) reserve, metabolic equivalents (METS), percentage METS, and absolute oxygen uptake may be obtained. For example, heart, rate intensity may be found by dividing the work by the total time of exercise.

The above-described method 400 for determining workload of a patient during exercise may be implemented by hardware, software, or firmware of a pacing system, such as the ICD described earlier with reference to FIGS. 1A and 1B, with particular reference to work detector 64.

Heart rate recovery involves analyzing how the heart recovers from a maximum rate during exercise. The heart rate recovery value may not change in a matter of days, but possibly in a matter of weeks. Obtaining the heart rate recovery value only during episodes of peak exercise, as opposed to any low-level exercise, may provide a more accurate reflection of cardiac health through heart rate recovery.

Figure 5:
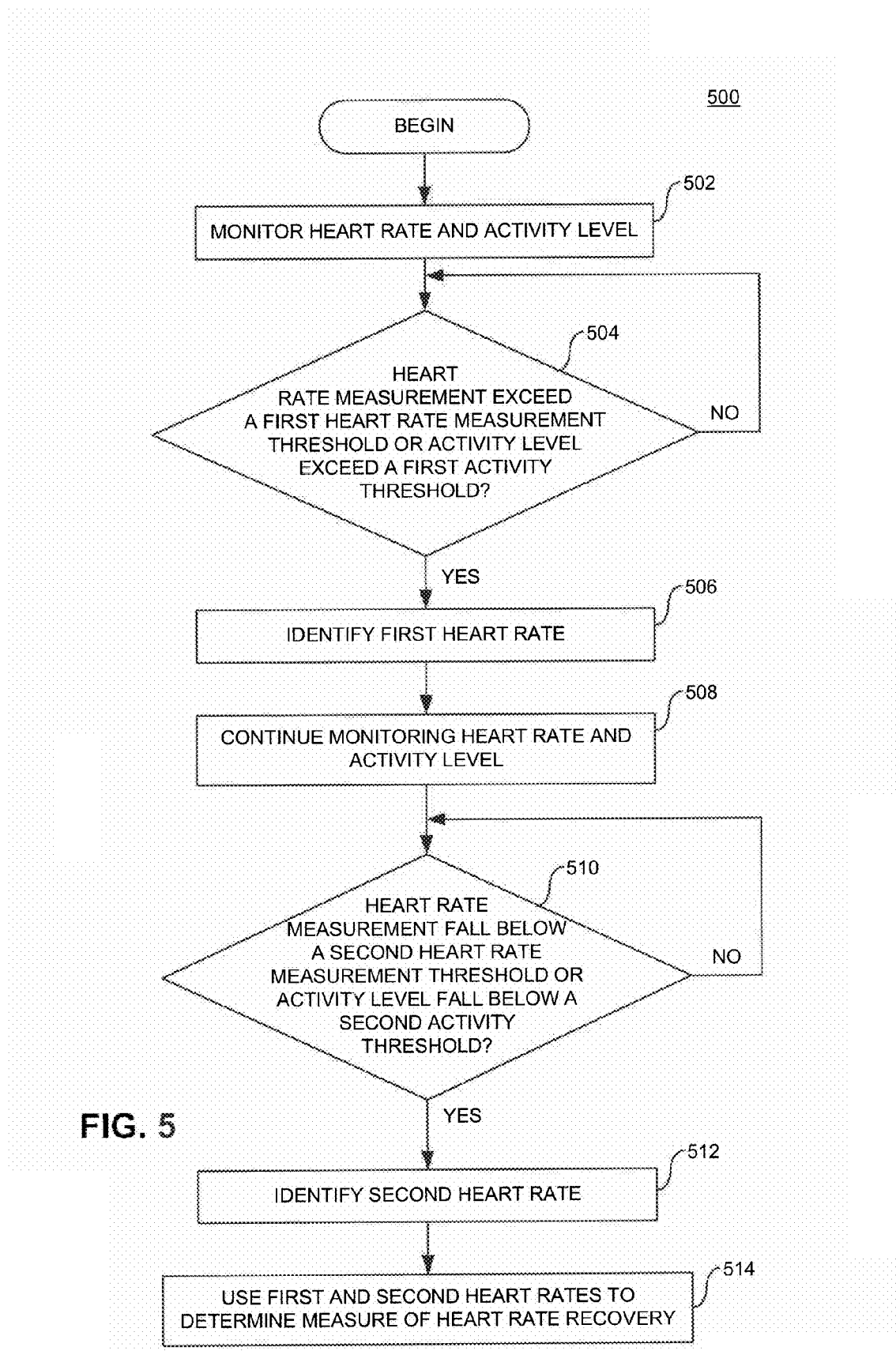
FIG. 5 is a flow chart illustrating an embodiment of a method for determining heart rate recovery of a patient after exercise.

A method 500 of determining a measure of heart rate recovery is illustrated in FIG. 5. According to an embodiment, the method 500 begins at step 502, in which the heart rate and activity level of the patient are monitored. The heart rate and activity level of the patient may be continuously monitored during the method 500. The heart rate and activity level can be monitored by any suitable method, including those discussed above.

Heart rate measurements can be produced based upon the monitored heart rate. As discussed above, such heart rate measurements include but are not limited to heart rate and heart rate intensity.

In step 504, a heart rate measurement is compared with a first heart rate measurement threshold, and an activity level is compared with a first activity threshold. The first heart rate measurement threshold and first activity threshold may be indicative of exercise, preferably vigorous or peak exercise.

In step 504, if a heart rate measurement exceeds a first heart rate measurement threshold, and/or an activity level exceeds a first activity threshold, then the method proceeds to step 506. In step 506, the heart rate is identified as a first heart rate. That is, the heart rate taken at the time (1) a heart rate measurement exceeded a first heart rate measurement threshold and/or (2) the activity level exceeded the first activity threshold is used as a first heart rate value for further computations.

In one embodiment, in step 504, the first heart rate is identified when at least one heart rate measurement exceeds the first heart rate measurement threshold. In another embodiment, the first heart rate is identified when at least one heart rate measurement exceeds the first heart rate measurement threshold for a predetermined period of time. In other embodiments, the first heart rate can be identified when an average value of heart measurements (taken over a predetermined time period, such as, for example, one minute) exceeds the first heart rate measurement threshold.

In another embodiment, the first heart rate can be identified when the activity level exceeds the first activity threshold. In yet another embodiment, the first heart rate can be identified when the activity level exceeds the first activity threshold for a predetermined period of time In still yet another embodiment, the first heart rate can be identified when for the predetermined period of time an average activity level exceeds the first activity threshold.

Preferably, the first heart rate is identified when both the activity level exceeds a first activity threshold and a heart rate measurement exceeds a first heart rate measurement threshold.

Even more preferably, the first heart rate is identified when the mean activity level value exceeds a first activity threshold for a predetermined period of time, and a mean heart rate measurement value, such as heart rate intensity, exceeds a first heart rate measurement threshold for a predetermined period of time.

In accordance with some embodiments, the first heart rate is identified only during peak exercise, only after a stringent set of conditions have been met. These conditions can include certain levels of heart rate intensity, activity level and duration of time. This first heart rate may be referred to as a peak exercise heart rate.

Illustratively, a peak exercise heart rate can be identified when the mean activity level exceeds a first activity threshold and the heart rate intensity exceeds a heart rate intensity threshold, such as, e.g., 80%, for a period of time of at least about five minutes.

As illustrated by step 508, heart rate and activity level continue to be monitored. It should be understood that the identified first heart rate can be overwritten by a subsequent heart rate (including a slower heart rate), provided that the first heart rate criteria described above are still met.

Heart rate and activity level also continue to be monitored, a illustrated by step 508, for determining the next parameter used to determine heart rate recovery, a second heart rate. The second heart rate is the heart rate after a slow-down in exercise, and is compared with the first heart rate to determine a measure of heart rate recovery. In accordance with some embodiments, heart rate measurements (such as for example heart rate) continued to be produced.

In step 510, a heart rate measurement is compared with a second heart rate measurement threshold, and an activity level is compared with a second activity threshold. The second heart rate measurement threshold and second activity threshold can be indicative of a slowing down or cessation of exercise.

If a heart rate measurement falls below a second heart rate measurement threshold, and/or an activity level falls below a second activity threshold, then in step 512 the monitored heart rate is identified as a second heart rate.

In one embodiment, the second heart rate is identified when the activity level falls below the second activity threshold for a predetermined period of time. Preferably, the second heart rate is identified when a mean activity level falls below the second activity threshold for a predetermined period of time. The comparison can also be done based on an average activity level over a predetermined period of time.

In another embodiment, the second heart rate is identified when a heart rate measurement falls below a second heart rate measurement threshold for a predetermined period of time. For example, if a heart rate measurement (e.g. heart rate) falls below a predetermined threshold and/or the mean activity level falls below a predetermined activity threshold, then the heart rate and activity levels can be recorded for a predetermined period of time, such as, for example one, two, or three minutes.

After the predetermined period of time, if a heart rate measurement is less than the heart rate measurement prior to the predetermined period of time, and the activity level is less than a third activity threshold (which can be the same as or lower than the second activity threshold), then a second heart rate is identified. Preferably, the slowest heart rate measured during the predetermined period of time is identified as the second heart rate.

In step 514, once a first heart rate and a second heart rate are identified, the first and second heart rates are used to determine a measure of heart rate recovery. For example, the second heart rate is subtracted from the first heart rate to obtain a heart rate difference. The difference is a heart rate recovery value.

It should be understood that additional second heart rate values can be identified after the first heart rate and compared to the first heart rate to determine a measure of heart rate recovery. Accordingly, the term "second heart rate" is intended to encompass one or more heart rates that meet the above-described criteria for identification of the second heart rate. In other words, the second heart rate may be several heart rates over consecutive periods of time (e.g. minutes).

Illustratively, heart rates measured at discrete times after the identified first heart rate and that meet the second heart rate identification criteria can be compared with the first heart rate to determine a measure of heart rate recovery. For example, the difference between the first heart rate and each of the second heart rates can provide a measure of heart rate recovery. Also, a listing of the first heart rate and heart rates meeting the second heart rate criteria as they decrease over time can also be a measure of heart rate recovery.

The invention also encompasses identifying the first heart rate at the time the criteria for identifying the second heart rate is met. For example, if a heart rate measurement exceeds a first heart rate measurement threshold or an activity level exceeds a first activity threshold, and subsequently a heart rate measurement falls below a second heart rate measurement or the activity level falls below a second activity threshold, a first heart rate can be identified at or near the inflection point between meeting the first and second heart rate identification criteria.

The second heart rate then can be identified as one or more heart rates measured subsequent to the identified first heart rate. For example, provided that the measured heart rates meet the second heart rate identification criteria, a second heart rate can be identified one minute, two minutes, and/or three minutes following the first heart rate. The difference between the first heart rate and the second heart rate at one, two, and/or three minutes post-first heart rate identification provides values that determine a measure of heart rate recovery.

To illustrate, a patient exercises (e.g. runs) for five minutes, and then stops running and sits down for three minutes. Provided that the patient met the first and second heart rate identification criteria described above, the first heart rate would be identified at the five minute mark, and the second heart rates would be identified at the six, seven, and eight minute mark. The first heart rate would be compared with each of the second heart rates at the six, seven, and eight minute mark to determine a measure of heart rate recovery.

Preferably, in the method 500 for determining a measure of heart rate recovery, heart rate measurements are filtered to remove noise and premature heart beats such as arrhythmias, PACs, and PVCs.

The above-described method 500 for determining the measure of heart rate recovery of a patient may be implemented in software, or firmware of a pacing system, such as the ICD described earlier with reference to FIGS. 1A and 1B, with particular reference to HR Recovery Detector 66.

Figure 6:
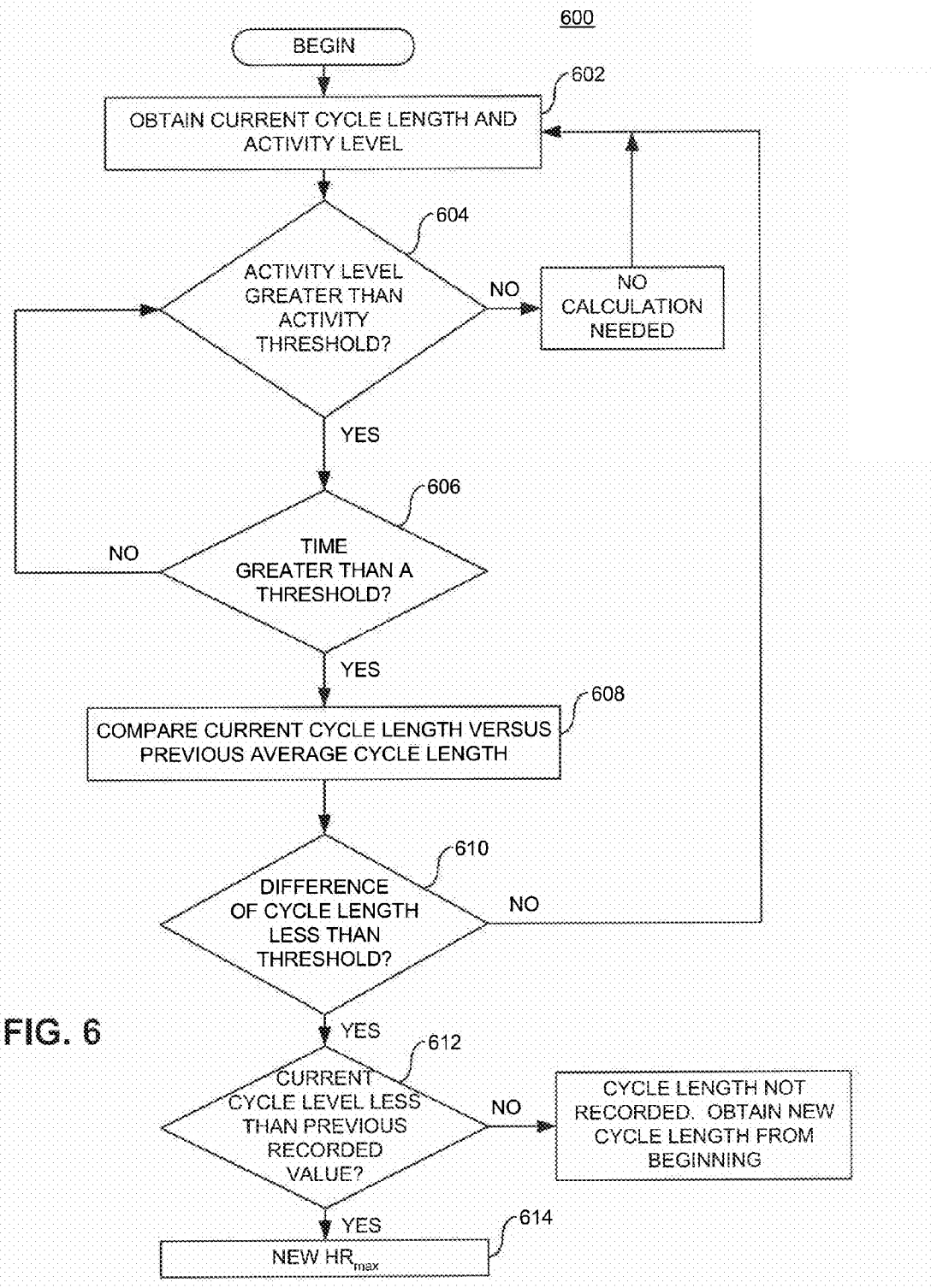
FIG. 6 is a flow chart illustrating another embodiment of a method for determining an observed maximum heart rate of a patient during exercise, as described in a first example.

A method for determining a maximum observed heart rate ($HR_{max}$) of a patient during exercise is illustrated in FIG. 6.

To calculate $HR_{max}$ for exercise conditioning, it is preferred that the patient has maintained a certain level of activity for a certain period of time. Thus, in the illustrative method, the maximum observed heart rate is not calculated unless the activity level is above a threshold activity for a certain period of time.

In method 600, the current cycle length (inverse of heart rate) and activity level are obtained as illustrated in step 602. It should be understood that the cycle length and activity level can be continuously or periodically monitored.

In step 604, the activity level measured is compared with an activity threshold. If the activity is less than an activity threshold, then the method returns to step 602. In this manner, steps 602 and 604 result in a continuous (or, optionally, periodic) monitoring of activity level.

If the measured activity level is greater than the activity threshold, then in step 606 the elapsed time (i.e., the period during which the activity level is greater than the activity threshold) is compared with a time threshold. The time threshold can be, for example, 2-3 minutes. Once this comparison indicates that sufficient time has elapsed, then step 608 is performed. Thus, before step 608 is performed, there has been a sufficient activity level for a sufficient period of time to indicate actual exercise by the patient.

In step 608, the current cycle length is compared with the previous cycle lengths, preferably a previous average cycle length. In step 610, if the difference of cycle length is too large (e.g., greater than or equal to about 100 milliseconds), this may indicate noise, PACs, PVCs or arrhythmias, and will not be identified as the $HR_{max}$. If this occurs, as illustrated in step 610, the method returns to step 602 to obtain a new, current cycle length and activity.

In step 610, if the difference of cycle length is less than a threshold (indicating that the current cycle length is not due to noise or a premature heart beat), then in step 612, the current cycle length is compared with the previous cycle length. If the current recorded cycle length is not less than the previously recorded value, then the current cycle length is not identified as the $HR_{max}$, and step 602 is repeated. However, if the current cycle length is less than the previous recorded value, then in step 614 the current cycle length is identified and stored as the new $HR_{max}$.

Figure 7:
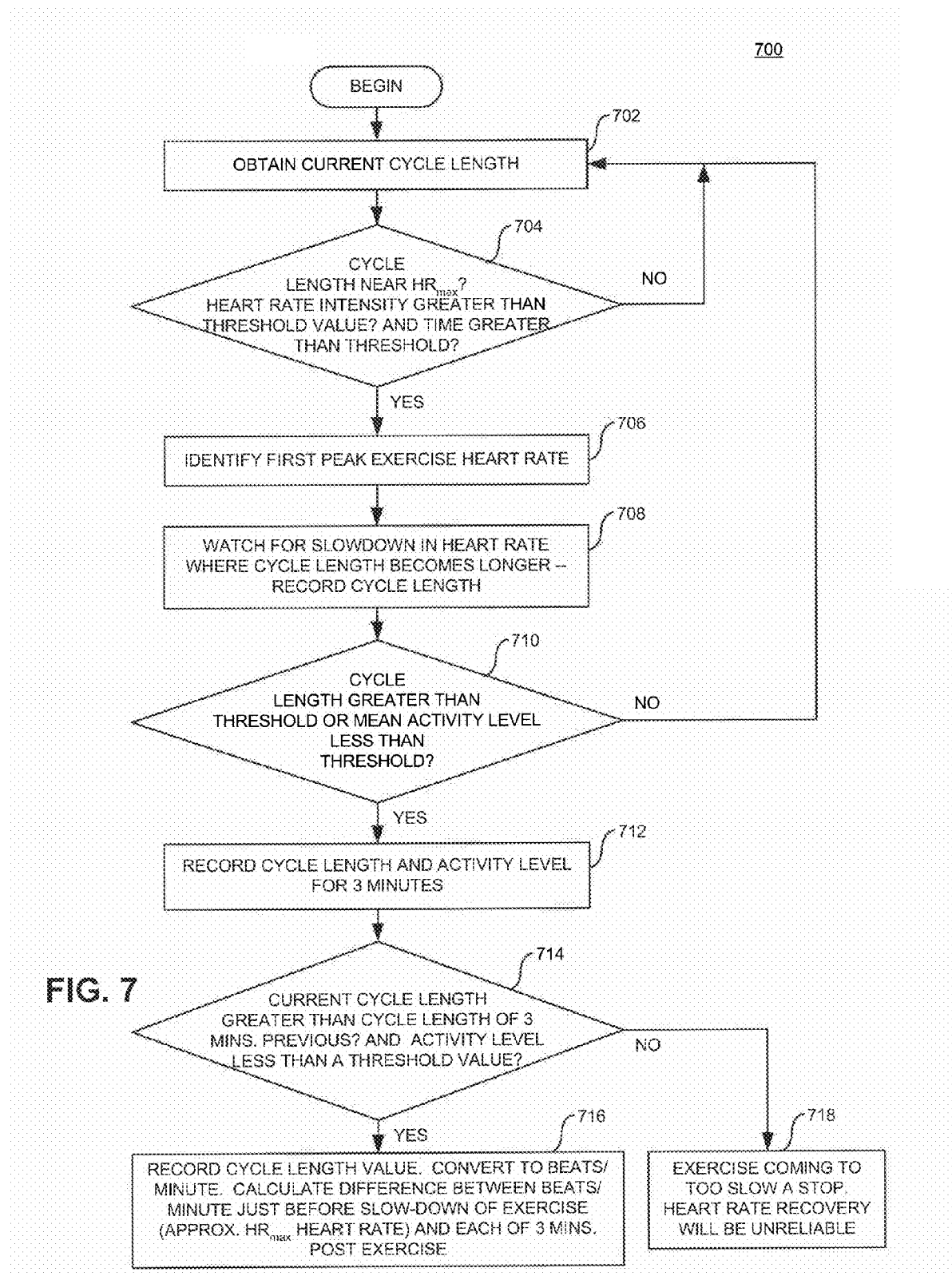
FIG. 7 is a flow chart illustrating another embodiment of a method for determining heart rate recovery of a patient, as described in a second example.

A method for determining heart rate recovery of a patient is illustrated in FIG. 7.

In accordance with the illustrated method 700, the first heart rate, a peak exercise heart rate is obtained by analyzing cycle lengths only when the qualifications for $HR_{max}$ have been met.

In step 702, the current cycle length is obtained. In step 704, if the cycle length is near $HR_{max}$, the value of the heart rate intensity is determined. If this value is greater than a predetermined threshold such as, e.g., 65%, and if the length of time is greater than a predetermined threshold, such as, e.g., 5 minutes, then in step 706 the cycle length is recorded as the first, peak exercise heart rate. Otherwise, the heart rate intensity for each cycle length continues to be determined.

The cycle length recorded in step 706 is continuously or periodically recorded, and may be overwritten by slower rates. However, if a noticeable slowdown occurs, in step 708 a new buffer collects the recorded cycle length. In step 710, if the current cycle length is greater than a predetermined threshold, such as, e.g., 20 milliseconds, or the mean activity level is less than a predetermined threshold, each indicative of a drop in activity, then in step 712 cycle length values are continuously recorded for three minutes.

In step 714, if after three minutes, the cycle length is greater than the cycle length measured three minutes previously, and the activity level is less than a threshold value, then in step 716 the largest cycle length for each of the three minutes is recorded as the second set of heart rate recovery values. If these criteria in step 714 are not met, then in step 718 a second heart rate is not recorded, as the exercise is coming too slowly to a stop.

Once the cessation of exercise has been determined, in step 716 both the first, peak exercise heart rate and the three heart rate recovery value cycle lengths are converted to beats per minute and subtracted from each other. The values obtained are the times of heart rate recovery.

Figure 8:
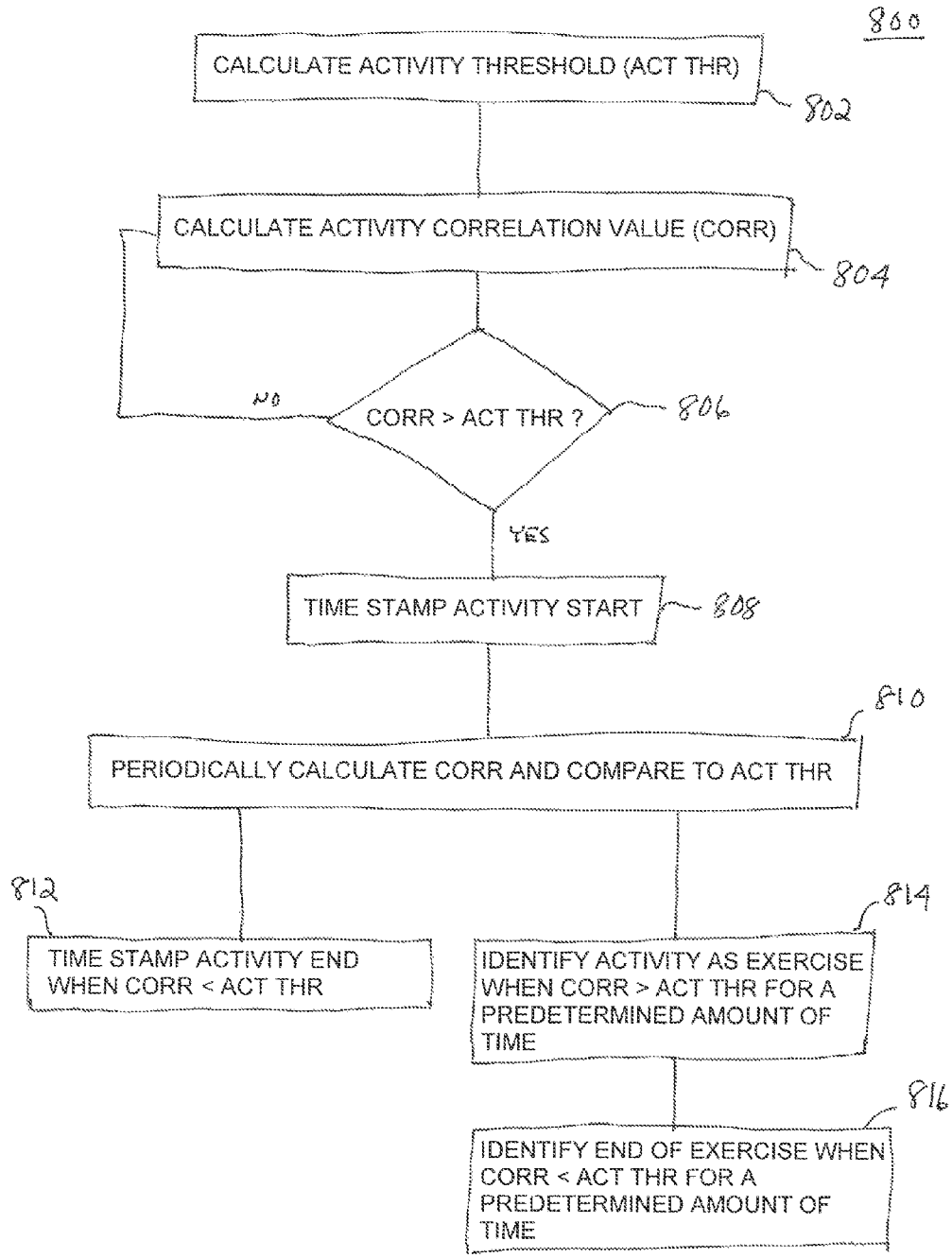
FIG. 8 is a flow chart illustrating an embodiment of a method for determining patient activity duration and exercise duration.

A method 800 of determining the duration of patient activity and patient exercise is illustrated in FIG. 8. According to an embodiment, the method 800 begins at step 802, in which a patient-specific activity threshold is calculated based on historical heart-rate data and historical activity-level data, which is collected over a period of time, and predetermined patient-specific offset parameters. Details related to the predetermination of patient-specific offset parameters and the determination of the patient-specific activity threshold are provided below with reference to FIGS. 9 and 10, respectively.

Continuing with FIG. 8, in step 804, current heart-rate and current activity level measurements are used to calculate a current activity correlation value ($CORR_{current}$) using the following equation:

$$CORR_{current} = HRR \times (ACT_{current} - ACT_{offset}),$$

where HRR (heart rate reserve) is obtained as described below with reference to FIG. 10, step 1008; $ACT_{current}$ is the activity measurement output by an activity sensor; and $ACT_{offset}$ is obtained as described below with reference to FIG. 9, step 908.

In a preferred embodiment, the heart rate and activity level measurements are taken periodically, for example, every "x" seconds or "n" heart beats where "x" and "n" are programmed and may be small quantities, such as 5 seconds and 3 heart beats, where resolution increases accuracy of detection. Periodic sampling is preferred over continuous measurements in order to conserve memory. In step 806, the current activity correlation value ($CORR_{current}$) is compared to the activity threshold (ACT THR). If the current correlation value does not exceed the activity threshold, the process returns to the step 804, where another current activity correlation value is calculated using the next periodic current heart-rate and activity level measurements, and the comparison process repeats. If at any time a current activity correlation value exceeds the activity threshold a beginning-of-activity time-stamp is created at step 808.

At step 810, the method continues to calculate current activity correlation values and compares each to the activity threshold. At step 812, if an activity correlation value fails to exceed the threshold, an end-of-activity time-stamp is created. As explained further below, the start and end time stamps provide a measure of the duration of activity. Numerous activity durations over a period of time may be used to report activity related quantities. For example, a total daily activity duration can, be created by summing all the periods of activity that occurred over the course of a day.

At step 814, if current correlation values continue to exceed the activity threshold value for a predetermined amount of time, the activity, is considered to have been sustained long enough to qualify as exercise. For example, assuming the predetermined amount of time is five minutes, 10 consecutive activity correlation values (calculated every 30 seconds) exceeding the activity threshold value would qualify the activit as exercise. The predetermined amount of time is programmable. As explained further below, if activity is identified as exercise, the predetermined amount of time associated with step 814 may be subsequently included in an exercise duration calculation.

At step 816, once an exercise state has been identified, the current correlation values continue to be monitored and if they fall below the activity threshold value for a predetermined amount of time the exercise period is considered to have ended. This predetermined amount of time which, is also programmable, serves to distinguish between a pause in exercise and a stop of exercise. For example, for a predetermined amount of time equal to one minute, at least six consecutive current correlation ($CORR_{current}$) values (calculated every 10 seconds) would have to fail to exceed the activity threshold to signify an end of exercise. Less than six current correlation values failing to exceed the activity threshold would be considered a pause in exercise. As explained further below, if an end of exercise is identified, the predetermined amount of time associated with step 816 may be subsequently included in an exercise duration calculation.

Figure 9:
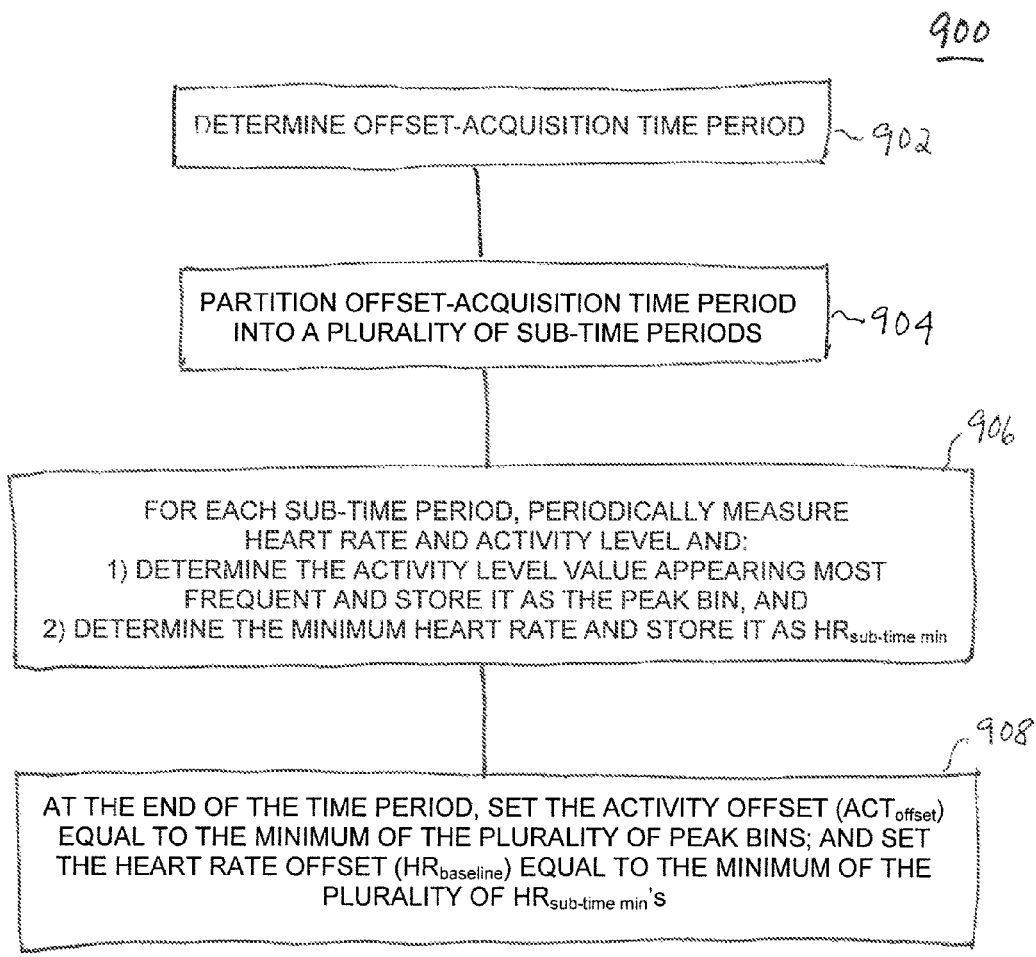
FIG. 9 is a flow chart illustrating an embodiment of a method for determining patient-specific offset parameters used in the method of FIG. 8.

With reference to FIG. 9, a method 900 of determining the patient-specific offset parameters ($ACT_{offset}$ and $HR_{baseline}$) is illustrated. The data collection of offset parameters are typically initiated upon implant of the device, and may be periodically updated to account for changes in the patient's condition and sensitivity of the device sensors. The method involves the collection and analysis of patient data over a period of time, referred to as the "offset-acquisition time period."

According to an embodiment, the method 900 begins at step 902, in which the offset-acquisition time period is determined. This time period may be programmed into the device by the physician and is long enough to allow for the collection and analysis of a quantity of patient data sufficient to avoid the potential for inaccurate parameter offset calculations due to possible noise and atypical patient activity. In one configuration, the offset-acquisition time, period is 24 hours. In step 904 the offset-acquisition time period is partitioned into sub-time periods, for example, 1 hour time periods in the case of a 24 hour offset-acquisition time period. Though the use of sub-time periods is not necessary, as will be apparent from the continuing explanation of the method 900, sub-time periods conserve memory space.

At step 906, for each sub-time period, heart rate and activity, level are periodically measured, for example every 10 seconds. The patient's heart rate may be determined by any suitable method. Many variations on how to determine heart rate are known to those of ordinary skill in the art, and any of these of reasonable accuracy may be used. Heart rate can be determined by measurement of an R-R interval cycle length (or P-P), which is the inverse of heart rate. As used herein, the heart rate (in beats per minute) can be seen as the inverse to cycle length, determined by 60,000 divided by the cycle length (in milliseconds).

The activity level of the patient may also be determined by any suitable method. For example, the activity level may be determined by an accelerometer, piezoelectric crystal, minute ventilation, or a derivative thereof, such as the sensor indicated rate. In one embodiment, activity level is determined using physiologic sensor 108. In this embodiment, sensor 108 is an accelerometer, a piezoelectric crystal or an impedance sensor.

Continuing with FIG. 9, step 906, for each sub-time period, in an exemplary type of activity data analysis, a histogram of activity level data over the sub-time period is created. At the end of the sub-time period, the activity level value appearing most frequent within the 1 hour histogram is saved as the "peak bin" and the rest of the activity data saved for the sub-time period is deleted from memory, thereby allowing the memory to be used again for the next sub-time period. In addition, at the end of each sub-time period, in an exemplary type of heart-rate data analysis, a minimum heart rate measured in the sub-time period is stored as $HR_{sub-time\ min}$. The $HR_{sub-time\ min}$ is not necessarily the lowest heart rate measured but instead may be a heart rate that is close to the lowest measured rate in order to account for possible noise.

At step 908, at the end of the time period, the activity offset parameter ($ACT_{offset}$) is determined to be the minimum of the plurality of activity-level "peak bins." The heart rate offset ($HR_{baseline}$) is determined to be the minimum of the $HR_{sub-time\ min}$'measured during the period of time.

Figure 10:
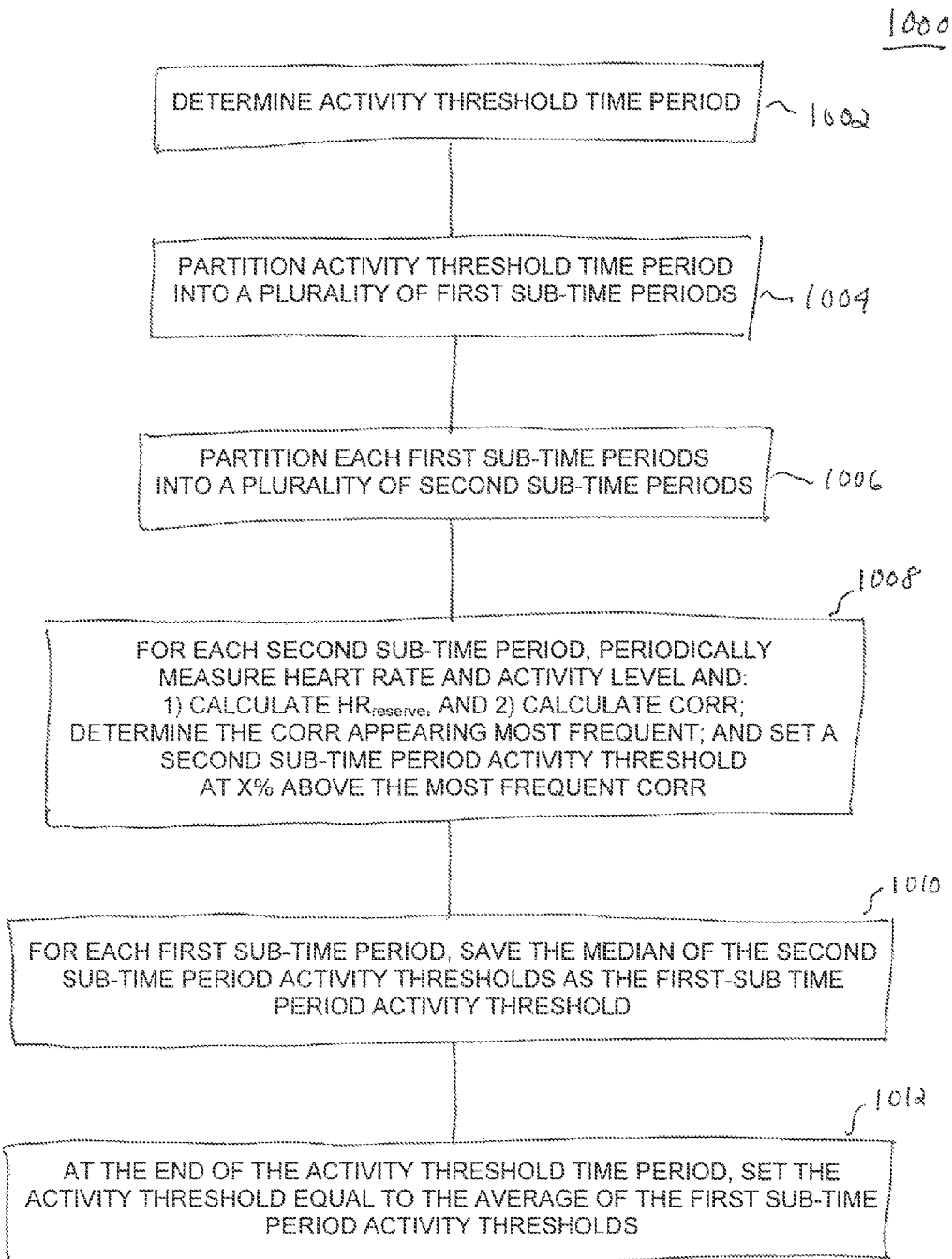
FIG. 10 is a flow chart illustrating an embodiment of a method for determining an activity threshold used in the method of FIG. 8.

With reference to FIG. 10, a method 1000 of determining the patient-specific activity threshold (ACT THR) of step 802 of the method of FIG. 8 is illustrated. The activity threshold is typically determined upon implant of the device, and may be periodically updated to account for changes in the patient's condition and sensitivity of the device sensors. The method involves the collection and analysis of patient data over a period of time, referred to as the "activity threshold time period."

According to an embodiment, the method 1000 begins at step 1002, in which the activity threshold time period is determined. This time period may be programmed into the device by the physician and is long enough to, allow for the collection and analysis of a quantity of patient data sufficient to avoid the potential for inaccurate activity threshold calculations due to possible noise and atypical patient activity. In one configuration, the activity threshold time period is 7 days. In step 1004 the activity threshold time period is partitioned into first sub-time periods, for example 1 day time periods, in the case of a 7 day activity threshold time period. In step 1006 the first sub-time periods are partitioned into second sub-time periods, for example, 1 hour time periods in the case of 1 day first sub-time periods. As described above with reference to the determination of patient-specific offset parameters, the use of sub-time periods is not necessary, but is preferred in order to conserve memory space.

At step 1008, for each second sub-time time period, heart rate and activity level are periodically measured, for example every 10 seconds. The heart rate measurements are used in turn, to calculate a plurality of heart-rate reserve values using the following equation:

$$HRR = \frac{HR - HR_{baseline}}{\text{Age Compensated Maximum } HR - HR_{baseline}} \times 100$$

Heart-rate reserve is used in the method instead of heart rate in order to utilize a heart rate measurement that is normalized across the patient population. Such normalization accounts for the fact that the same heart rate may correspond to different activity states for different people. For example, a heart rate of 90 beats per minute may correspond to sitting for one person and walking for another person. In the equation indicated above, HR (heart rate) may be obtained by any suitable method; $HR_{baseline}$ may be obtained as described with reference to FIG. 9, and age compensated maximum heart rate can be calculated by the formula: (220-age).

While the above HRR equation is expressed in terms of HR parameters, actual implementation of the above HRR equation may involve the use of heart rate interval (HRI) calculations. In terms of HRI, the equation for HRR becomes:

$$HRR = \frac{\frac{HRI_{min}}{HRI} \times (HRI_{baseline} - HRI)}{HRI_{baseline} - HRI_{min}} \times 100$$

In the equation indicated above, HRI (heart rate interval) may be obtained by any suitable method; $HRI_{min}$ may be obtained using the equation: 60,000/(220-age) and $HRI_{baseline}$ may be obtained by converting the $HR_{baseline}$ measurement described with reference to FIG. 9 into a heart rate interval measurement.

In order to reduce rounding errors when processing the above equation, it is desirable to perform all multiplication functions first in order to make the numerator larger than the denominator. Considering the range of HRI in milliseconds, a 2 byte by 2 byte multiplier may be required to perform the multiplication operations. In addition, there are several multiplication and division operations in the HRR equation, which may impact processor duty cycle.

In an alternate embodiment, processing efficiency may be enhanced by obtaining an approximated heart-rate reserve using the following equation:

$$HRR_{approx} = HR - HR_{baseline}$$

which in terms of HRI translates to:

$$HRR_{approx} = (60,000/HRI) - (60,000/HRI_{baseline})$$

This calculation reduces the number of arithmetic operations and may be completed using a 1 byte by 1 byte multiplier; thereby reducing the processor duty cycle.

Continuing with step 1008, the activity level measurements are used, in turn to calculate a plurality of activity correlation values using the following equation:

$$CORR_{sub-time} = HRR \times (ACT_{sub-time} - ACT_{offset})$$

where $ACT_{sub-time}$ is the activity measurement provided by the activity sensor during the sub-time period; and $ACT_{offset}$ is obtained as described above with reference to FIG. 9, step 908. Note that $HRR_{approx}$ may be used in place of HRR in the $CORR_{sub-time}$ calculation.

Figure 11:
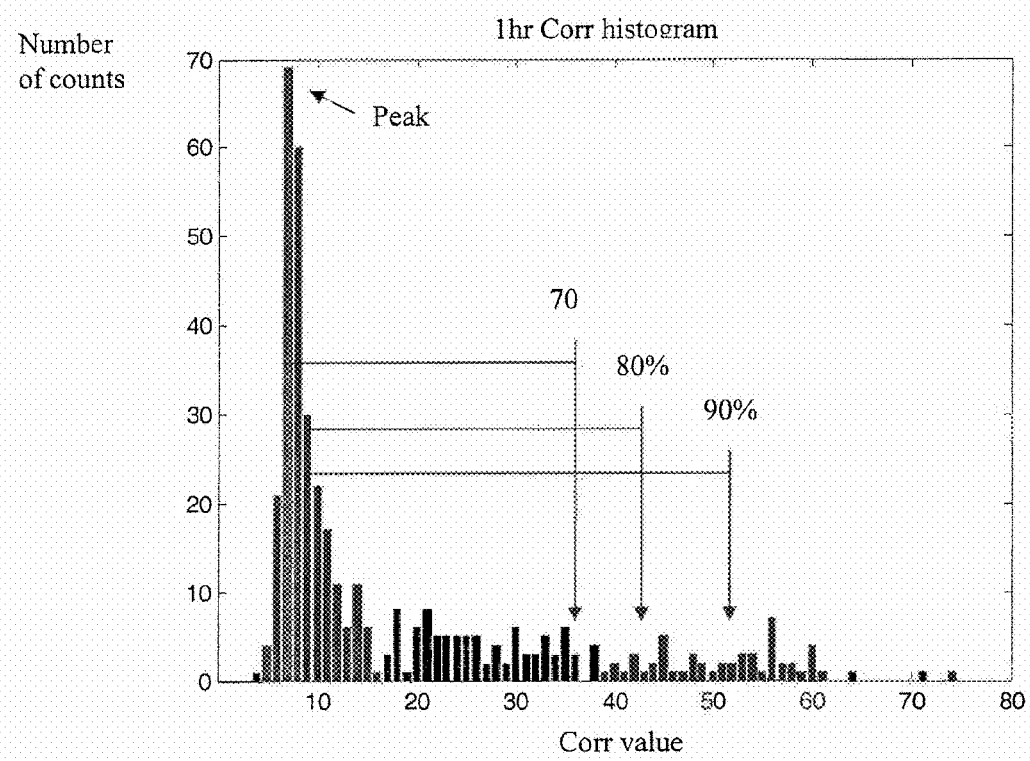
FIG. 11 is an example of a histogram of activity correlation values that may be used to determine the activity threshold used in the method of FIG. 8.

The sub-time correlation values are analyzed using, for example, a histogram analysis similar to that described above with respect to FIG. 9, step 906, to identify the sub-time correlation value appearing most frequent within the second sub-time period. A second sub-time activity threshold is set at X % above the most frequent correlation value, where X is programmable and may be for example, 70, 80 or 90. Setting the second sub-time activity threshold as a percentage above the most frequent correlation value provides for the filtering of noise and allows for a deterministic approach towards a threshold that encompasses a level of activity. An example of a 1 hour histogram is shown in FIG. 11.

Continuing with FIG. 10, in step 1010 after identifying the plurality of second sub-time period activity thresholds, e.g., twenty-four, 1 hour thresholds in the case of a 1 day first sub-time period, the median of the plurality of second sub-time period activity thresholds is identified as the activity threshold for that first sub-time period. While other statistical measurements may be used, the median value is chosen for robustness of the threshold, which will not be changed by several hours of atypical activities. The process is repeated for each first sub-time period to identify a plurality of first sub-time period activity thresholds. Thus in the case of a 7 day activity threshold time period, seven, 1 day activity thresholds would be determined. In step 1012, at the end of the total activity threshold time period, e.g., 7 days, the activity threshold (ACT THR) is set equal to the average of the plurality of first sub-time period, e.g., 1 day, activity thresholds. While other statistical measures may be used, an average is chosen to account for weekday and weekend difference of activity patterns.

Figure 12:
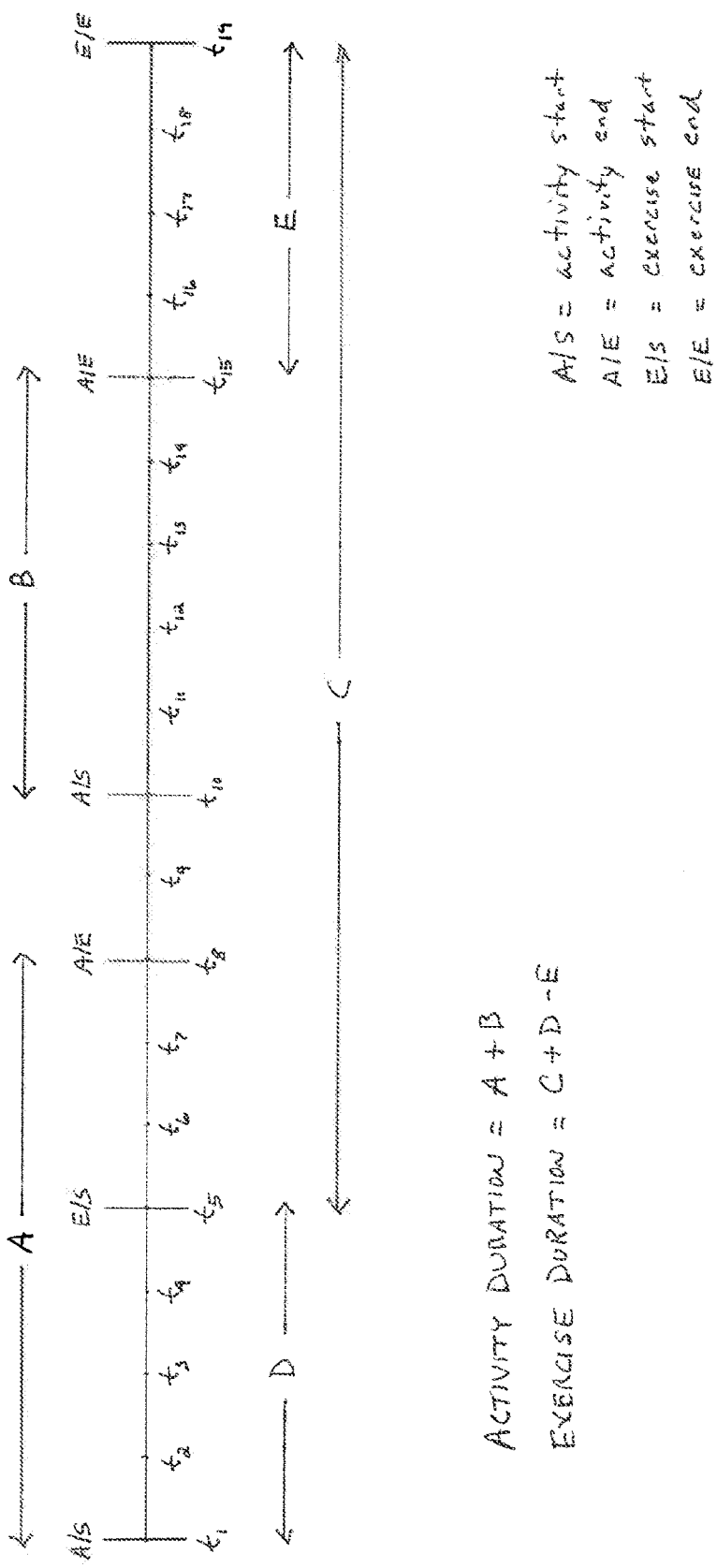
FIG. 12 is an exemplary time line illustrating the start and end of activity and exercise time periods.

With reference to FIG. 12, various activity and exercise states identified over a period of time in accordance with the method 800 described above with reference to FIG. 8 is presented in a time line to aid in describing possible activity duration and exercise duration calculations. At time $t_1$, $CORR_{current}$ exceeds ACT THR and a start of activity (NS) is identified. For each of times $t_2$ through $t_7$, CORR exceeds ACT THR. The time $t_1$ through $t_5$ corresponds to the predetermined "exercise" time used to identify exercise; accordingly, a start of exercise (E/S) is identified at time $t_5$.

At time $t_8$ CORR did not exceed ACT THR and an end of activity (A/E) is identified. At time $t_{10}$ CORR again exceeds ACT THR and a start of activity (A/S) is identified. Because the time between $t_8$ (when CORR first failed to exceed ACT THR) and $t_{10}$ (when CORR again exceeded ACT THR) is less that the predetermined time used to identify the end of exercise (an "exercise hysteresis"), this period of time is considered to be a pause in exercise and there is no end of exercise identification. At time $t_{15}$, CORR failed to exceed ACT THR and an end of activity (A/E) is identified. At each of times $t_{16}$ through $t_{19}$, CORR fails to exceed ACT THR. Because the time between $t_{15}$ and $t_{19}$ corresponds to the predetermined time used to identify the end of exercise, an end of exercise (E/E) is identified at time $t_{19}$.

From the start and end identifications included in this exemplary time line, activity duration would be calculated as A+B where A is the duration of the first activity period and B is the duration of the second activity period. Exercise duration would be calculated as C+D−E, where C is the difference between the start of exercise (E/S) and the end of exercise (E/E), D is the predetermined time used to identify the start of exercise and E is the predetermined time used to identify the end of exercise.

With reference to FIGS. 13A-13D, benefits of the invention are noted upon comparison of various graphs of measured quantities as a function of time during Stairmaster and treadmill exercises. To ensure a meaningful comparison, the graphs are based on exercise activity of the same patient, with similar exercise timing and intensities. The measured quantities include a heart-rate based measurement, e.g., HR reserve, and an activity measurement obtained using a one-dimensional physiological sensor oriented to detect horizontal movement but not vertical movement.

Figure 13A:
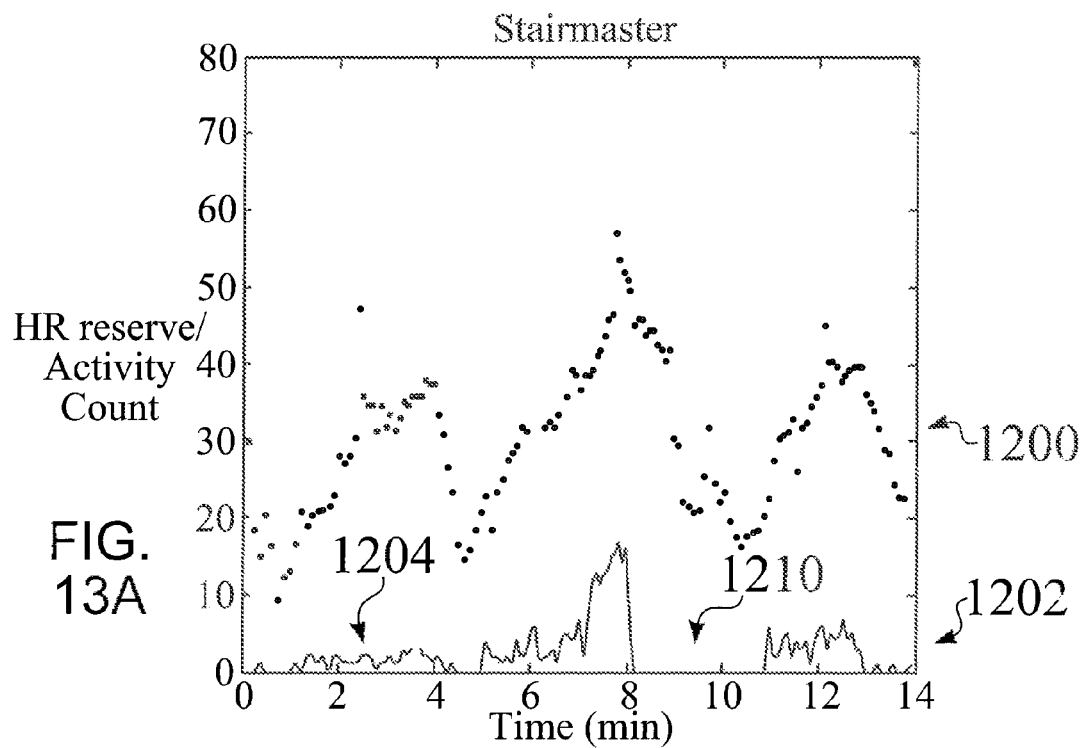
FIG. 13A is a graph of heart rate reserve data and activity sensor data as a function of time corresponding to patient activity on a Stairmaster.
Figure 13B:
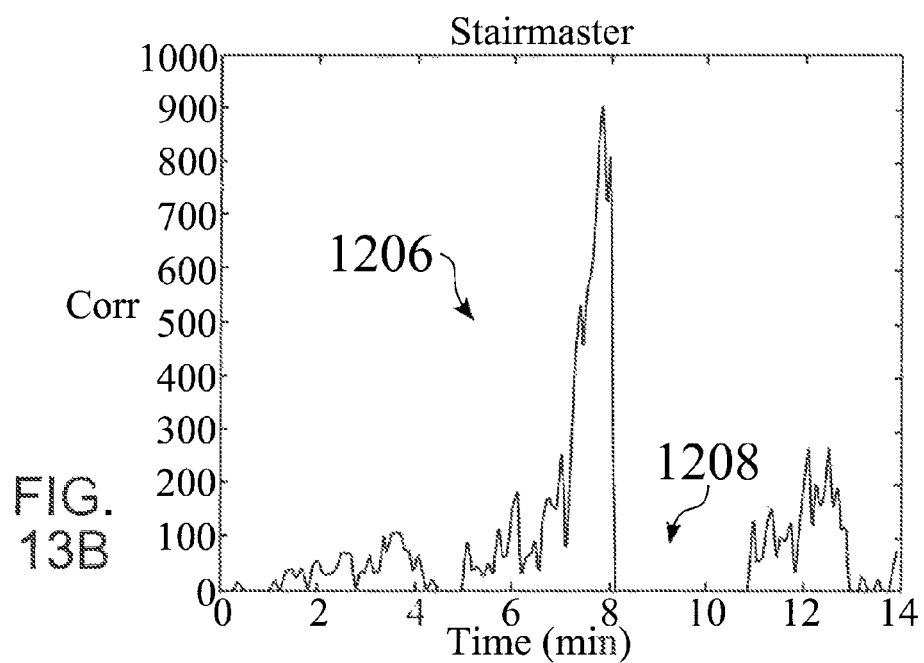

As shown in FIG. 13A, because of the vertical movement associated with Stairmaster exercise, there is a significant disparity between the magnitude of heart-rate based measurements 1200 and activity-sensor based measurements 1202. Notice that using activity sensor data only, Stairmaster exercise may not be detected at all due to low level activity measurements 1204. From FIG. 13B it is noted that using a correlation value (Corr) 1206, which corresponds to a combination of the heart rate measurements and activity measurements of FIG. 13A, allows for better detection of Stairmaster exercise despite its low-level activity measurements. It is also noted that the correlation value is not influenced by a relatively high heart rate measurement. In other words, if there is no activity but only a high heart rate, the correlation value will not be influenced. This is evident in FIG. 13B near the 8 minute mark 1208 where the graph indicates zero exercise consistent with the zero activity indicated near the 8 minute mark 1210 in FIG. 13A.

Figure 13C:
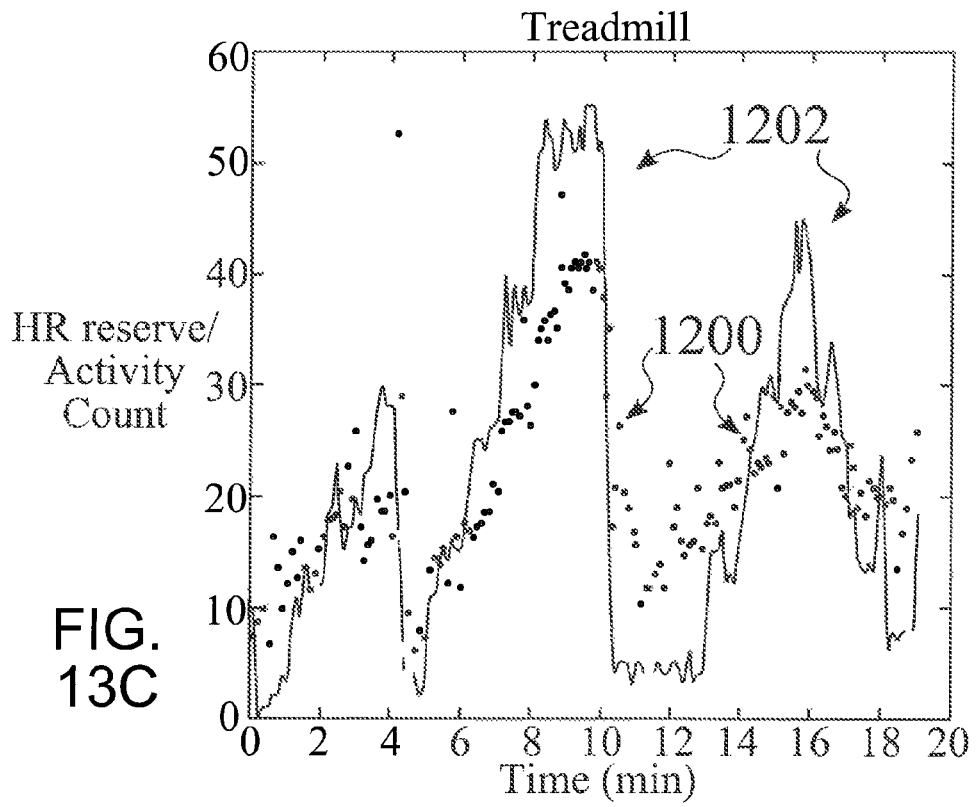
FIG. 13C is a graph of heart rate reserve data and activity sensor data as a function of time corresponding to patient activity on a treadmill.
Figure 13D:
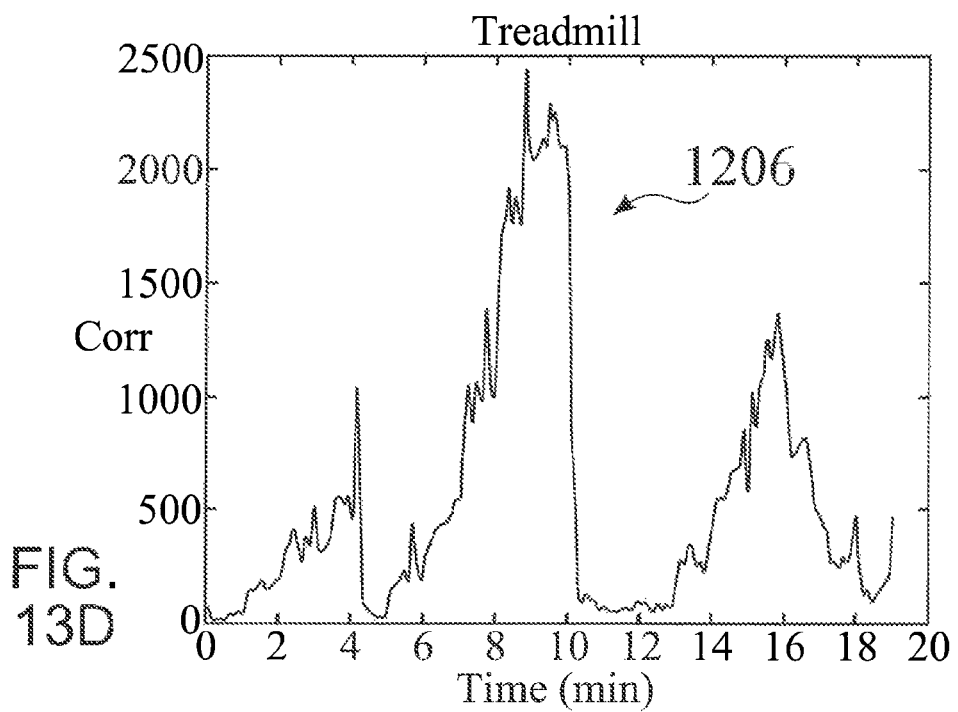
FIG. 13D is a graph of correlation values as a function of time corresponding to the same patient activity on a treadmill shown in FIG. 12c.

With reference to FIG. 13C, because of the horizontal movement associated with treadmill exercise, the disparity between the magnitude of heart-rate based measurements 1200 and activity-sensor based measurements 1202 is less pronounced than in the Stairmaster graph in FIG. 13A. The correlation value measurements 1206 plotted in FIG. 13D correspond well with the heart-rate based measurements 1200 and activity-sensor based measurements 1202 of FIG. 13C. From the foregoing graphs it is noted that using the correlation value (Corr) allows for better detection of varying forms of exercise, regardless of the tendency of the exercise to involve horizontal or vertical movement.

As previously described, automatic determination of the activity threshold may involve a scaling factor X %, which may be for example, 80% above a correlation value arrived at using a histogram of historical patient data. For some people, however, this predetermined or default scaling factor may result in an over-sensitive activity threshold that causes the algorithm to consider a patient's daily activity such as office work, reading and talking as significant activity, or conversely, an under-sensitive threshold value that causes the algorithm to exclude significant activity, such as walking, from its exercise diagnostic routine. Therefore, verification, recalibration or optimization of the activity threshold may be desirable.

One process for optimizing the activity threshold is based on a comparison of activity duration measurements provided by the patient device using the existing activity threshold and corresponding activity duration measurements provided by means external to the patient. Respective duration measurements for activity expected not to be considered significant activity are obtained from the patient device and the external means. Alternatively, or in addition, respective duration measurements for low-level activity, which although low, is still expected to be considered significant activity, may be obtained from the patient device and the external means.

Depending on the correspondence between the one or more patient-device measurements and the one or more external-means measurements, an adjustment of the activity threshold may be warranted For example, for non-significant activity expected to be undetected by the patient device, a patient-device measurement greater than zero may be an indication of an over-sensitive activity threshold, i.e., a threshold that is set too low. Accordingly, an increase in the activity threshold may be warranted. The magnitude of the increase may be based on the difference between the patient-device measurement and external means measurement, with the magnitude of the increase, increasing as the difference between the measurements decrease.

Below is a table of hypothetical patient-device measurements for non-significant patient activity, e.g., desk work, talking, etc. that occurred for a period of 10 minutes. In order to ensure accurate results, the non-significant activity is continuous for the entire period. In other words, the activity of the patient does not deviate into either low-level significant activity, such as light walking, or no activity at all. The table also includes a measurement of the percentage difference between the patient-device measurement and the known duration of significant activity, and corresponding suggested activity threshold adjustments. The known duration of significant activity is provided by an external measurement device, and is 0 minutes, i.e., 10 minutes of known non-significant patient activity corresponds to 0 minutes of significant activity. For ease in presentation, duplicate measurements are included, e.g. 0.5 min, 3.0 min and 6.0 min, across table rows. In practice however, a measurement would correspond to only one row. Thus, for example, the 0.5 minute upper limit in the first row may be "less than or equal to" 0.5 minute, while the 0.5 minute lower limit in the second row may be "greater than" 0.5 minute.

| External-device measurement of significant activity | Patient-device measurement of significant activity | % diff | Suggested threshold change |
|---|---|---|---|
| 0 min | 0–.5 min. | ~0 | 0% |
| 0 min | .5–3.0 min. | ≦30 | +5% |
| 0 min | 3.0–6.0 min | 30–60 | +10% |
| 0 min | 6.0–10 min | 60–100 | +15% |

For low-level activity expected to be detected by the patient device, a patient-device measurement less than the known duration of the activity may be an indication of under detection by an under-sensitive activity threshold, i.e., a threshold that is set too high. Accordingly, a decrease in the activity threshold may be warranted. The magnitude of the decrease may be based on the difference between the patient-device measurement and external means measurement, with the magnitude of the decrease, increasing as the difference between the measurements increase.

Below is a table of hypothetical patient-device measurements for low-level significant patient activity, e.g., light walking, that occurred for a period of 10 minutes. In order to ensure accurate results, the low-level significant activity is continuous for the entire period. In other words, the activity of the patient does not deviate into either non-significant activity or mid to high-level significant activity. The table also includes a measurement of the percentage difference between the patient-device measurement and the known duration of low-level significant activity, and corresponding suggested activity threshold adjustments. The known duration of low-level significant activity is provided by an external measurement device, and is 10 minutes. As with the previous table, for ease in presentation, duplicate measurements are included, e.g. 9.0 min, 7.5 min and 2.5 min, across table rows.

| External-device measurement of significant activity | Patient-device measurement of significant activity | % diff | Suggested threshold change |
|---|---|---|---|
| 10 min | 9.0-10 min. | <10 | 0% |
| 10 min | 7.5-9.0 min | 10-25 | −5% |
| 10 min | 2.5-7.5 min | 25-75 | −10% |
| 10 min | 0-2.5 min | 75-100 | −15% |

Figure 14:
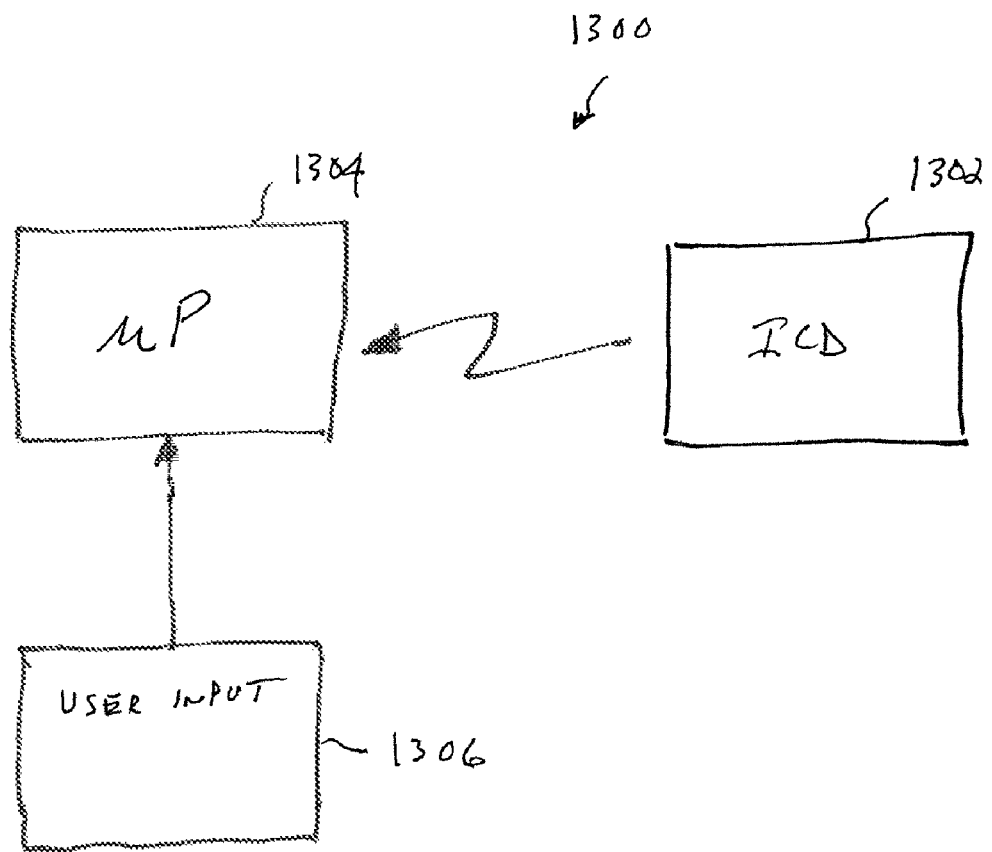
FIG. 14 is a functional block diagram of a system including a prediction model for optimizing an existing activity threshold.

With reference to FIG. 14, an exemplary system 1300 for optimizing the activity threshold includes a patient-associated medical device, such as an ICD 1302 and an external processor or programmer 1304. The external processor 1304 includes an input for receiving data from the ICD 1302. Such data may be interrogated from the ICD using a telemetry wand or by RE telemetry means. The external processor 1304 also includes an input for receiving data other than from the ICD. Such data may be provided through a user interface 1306, e.g., a keyboard, and may include data related to external-means measurements. For example, an activity session of a patient may be monitored by a physician using a timer and the duration of the activity may be input to the processor 1304 through a keyboard. The user interface may also include a perception device capable of providing a perceptible indication, e.g., visual, sound, of any suggested adjustments to the activity threshold.

A prediction model is programmed in the processor 1304. This model processes measurements from the patient-device 1302 and measurements from external means related to patient activity in a manner described above and provides adjustments to the activity threshold. These adjustments may be in the form of suggested increases or decrease in activity threshold values provided to the physician on a display of the user input device 306, in which case the physician ultimately decides whether the suggested change will be implemented. Alternatively, these adjustments may be telemetrically communicated to the patient device 1302, in which case the changes may be automatically implemented by the patient device.

Figure 15:
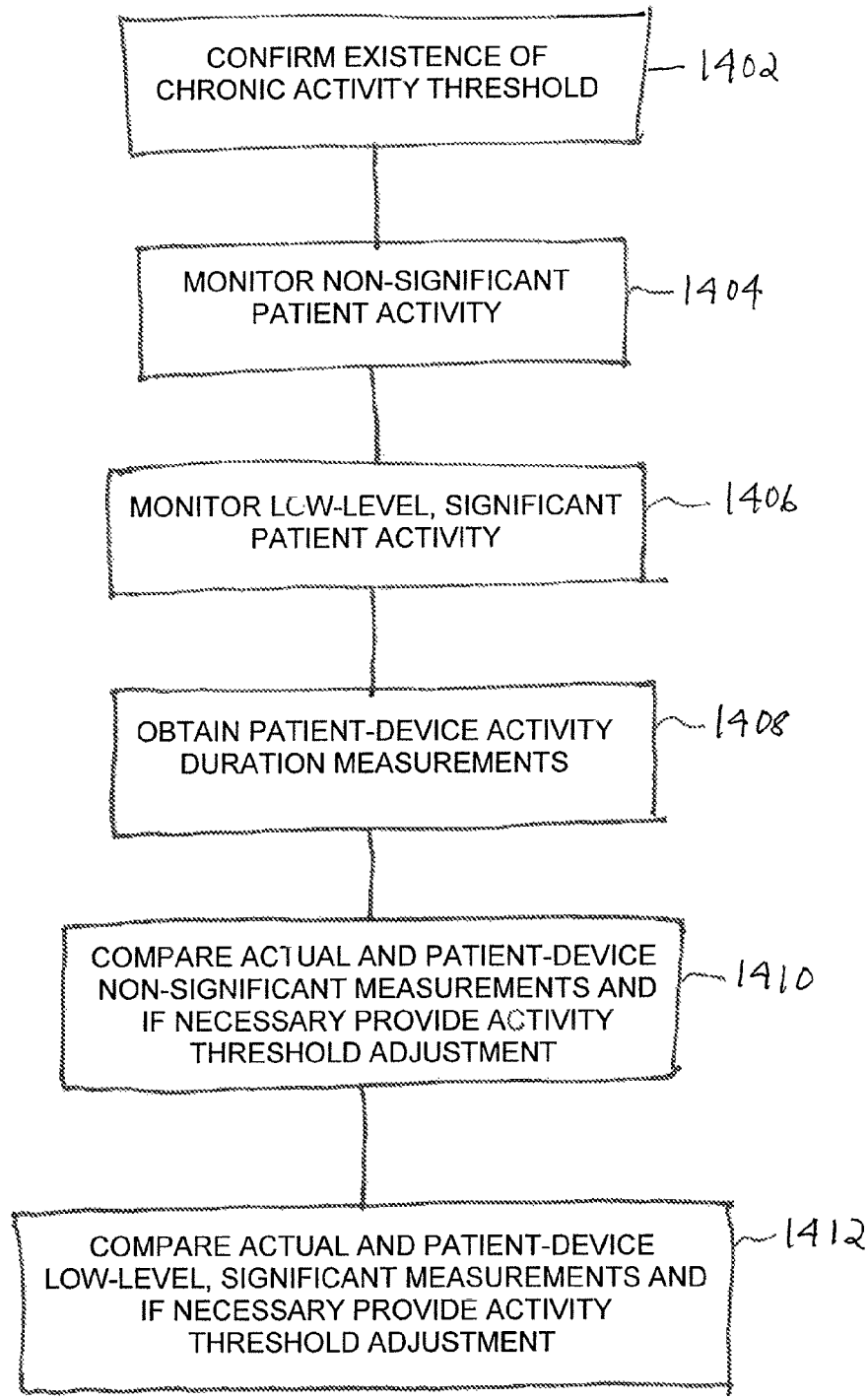
FIG. 15 is a flow chart illustrating an embodiment of a method for optimizing an activity threshold.

With reference to FIG. 15, a method 1400 of ensuring optimization of the activity threshold is illustrated. In block 1402 communication between an ICD and, external processor is established and the ICD is, interrogated to confirm the existence of a chronic activity threshold. A chronic activity threshold may be the initial activity threshold determined by the ICD after implant (as described above with reference to FIG. 10) or a threshold previously obtained using the predication model.

If a chronic activity threshold exists the process proceeds to block 1404 where non-significant patient activity is monitored. For example, the patient may initiate and continue non-significant activity, e.g., desk work, talking, for a specified period of time. The actual duration of the non-significant activity, as provided by external means, is input to the programmer. In block 1406, low-level, significant patient activity is monitored. For example, the patient may initiate and continue low-level, significant activity, e.g., light walking, for a specified period of time. The actual duration of the low-level, significant activity is input to the programmer. It is understood that the order in which the activity types are initiated is arbitrary, in that low-level, significant activity may be initiated prior to non-significant activity.

At block 1408, activity duration measurements for both the non-significant and the low-level, significant activity are obtained from the ICD. At block 1410, the predication model compares the non-significant activity duration measurement from the ICD with the actual measurement from the external means and if necessary, provides a suggested scaling factor for the threshold based on the correspondence between the measurements. At block 1412, the prediction model compares the significant activity duration measurement from the ICD with the actual measurement from the external means and, if necessary, provides a suggested scaling factor for the activity threshold based on the correspondence between the measurements.

Exemplary scaling factors for increasing and decreasing the activity threshold are provided in the previously described tables. Numerous other scaling schemes may be within the purview of those of ordinary skill in the art. Accordingly, the invention is in no way limited to the scaling schemes presented in the tables.

Figure 16A:
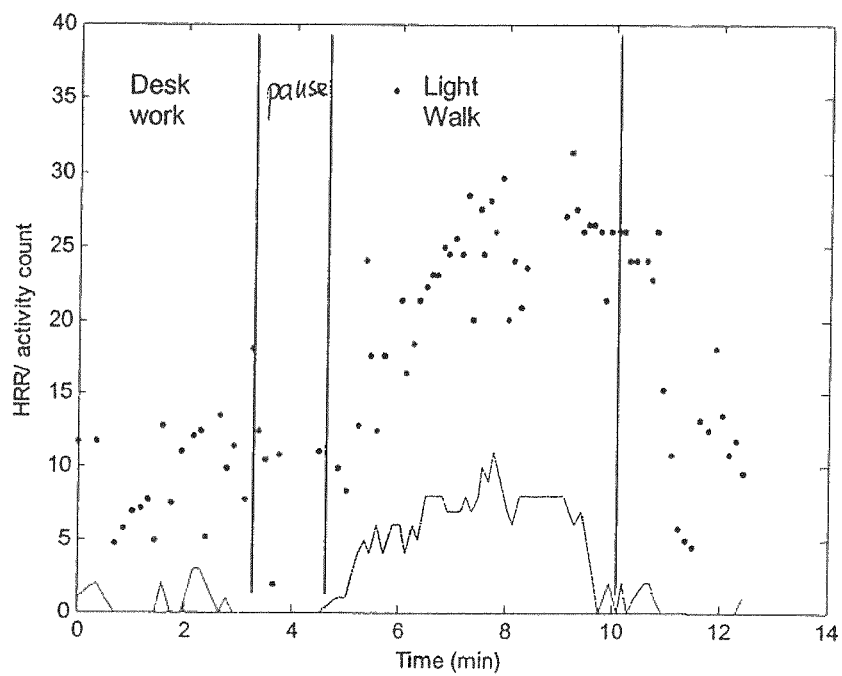
FIG. 16A is a graph of heart rate reserve and activity sensor measurements as a function of time for a period of expected, non-significant patient activity.
Figure 16B:
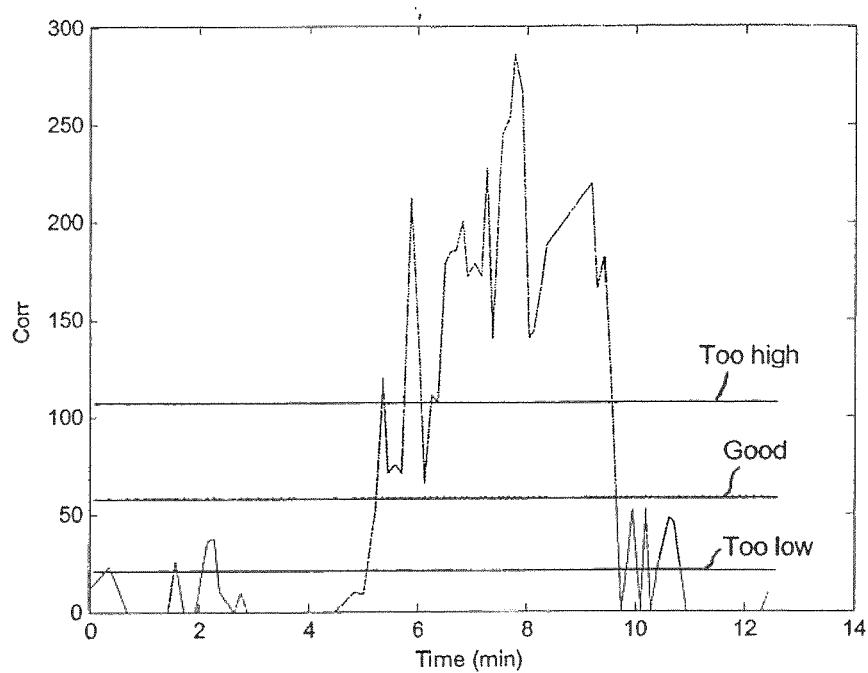
FIG. 16B is a graph of correlation values derived from the heart rate reserve and activity sensor measurements of FIG. 16A, as a function of time and including examples of different activity thresholds.

With reference to FIG. 16A, heart rate reserve (HRR) measurements (indicated by dots) and activity sensor measurements (indicated by lines) are plotted as a function of time for a period of non-significant activity, e.g., desk work and a period of low-level significant activity, e.g., light walk, with a pause included between the two periods. In FIG. 16B, correlation values (CORR) derived from the HRR and activity data of FIG. 16A are plotted as a function of time. Different activity threshold values (horizontal lines), including one considered too high (resulting in undesirable non-detection of low-level significant activity), one considered too low (resulting in undesirable detection of non-significant activity) and one considered good (resulting in detection of low-level significant activity and non-detection of non-significant activity.

It will be appreciated by those skilled in the art that the above methods 200, 400, 500, 600, 700, 800 and 1400 can be used within the hardware, software, and/or firmware of a pacing system, such as the ICD described earlier with reference to FIGS. 1A and 1B, for example.

Example embodiments of the methods, systems, and components of the present invention have been described herein. As noted elsewhere, these example embodiments have been described for illustrative purposes only, and are not limiting. Other embodiments are possible within the scope of the invention. Such embodiments will be apparent to persons skilled in the relevant art(s) based on the teachings contained herein. For example, while the prediction model has been described as residing within and being executed by an external processor, the model may instead reside in memory within a patient device. In this case, the model could be initiated externally and executed using patient-device duration measurements stored within the device and external-means duration measurements transmitted to the patient device. Also, while the description of the prediction model has focused on implantable patient devices, the invention may find application in external patient devices.

Thus, the breadth and scope of the present invention should not be limited by any of the above-described exemplary embodiments, but should be defined only in accordance with the following claims and their equivalents.

The invention claimed is:

1. A system comprising:
 a patient-associated medical device operative to detect patient activity based on a programmable activity threshold, to determine the duration of detected activity, and to output data indicative of the duration; and
 a processor operative to:
  receive first duration data from the medical device indicative of first duration measurements for each of a first activity session and a second activity session;
  receive second duration data indicative of second duration measurements for each of the first activity session and the second activity session, the second duration measurements based on actual start and stop of the activity sessions; and
  suggest an adjustment of the activity threshold based on at least one of correspondence between the first duration measurement and the second duration measurement of the first activity session, and correspondence between the first duration measurement and the second duration measurement of the second activity session.

2. The system of claim 1 wherein the patient-associated medical device is an implantable device.

3. The system of claim 1 wherein the processor is included in an implantable device.

4. The system of claim 1 further comprising a user interface operative to provide the second duration data.

5. The system of claim 4 wherein the user interface is further operative to provide a perceptible indication of the suggested adjustment.

6. The system of claim 1 wherein the first activity corresponds to activity expected to be undetected and the processor is operative to suggest an increase in the activity threshold when first activity is detected.

7. The system of claim 1 wherein the second activity corresponds to activity expected to be detected and the processor is operative to suggest a decrease in the activity threshold when second activity is under detected.

8. The system of claim 1 wherein the processor is further operative to automatically adjust the activity threshold.

9. A system associated with a patient-associated medical device operative to detect patient activity based on a programmable activity threshold and to determine the duration of detected activity, said system comprising:
 means for obtaining first and second duration measurements for at least one of a first activity session and second activity session, the first duration measurement based on the activity threshold, the second duration measurement based on actual start and stop of the activity session; and
 means for suggesting an adjustment of the activity threshold based on at least one of correspondence between the first duration measurement and the second duration measurement of the first activity session, and correspondence between the first duration measurement and the second duration measurement of the second activity session.

10. The system of claim 9 wherein means for suggesting comprises means for automatically reprogramming the activity threshold to correspond with the adjustment.

11. The system of claim 9 wherein means for suggesting comprises means for providing a perceptible indication of the adjustment.

* * * * *